US012806187B2

(12) United States Patent
Lorico et al.

(10) Patent No.: US 12,806,187 B2
(45) Date of Patent: Nov. 24, 2026

(54) USE OF TRIAZOLE ANALOGUES FOR INHIBITION OF A TRIPARTITE VOR PROTEIN COMPLEX IN MULTICELLULAR ORGANISMS

(71) Applicants: Aurelio Lorico, Las Vegas, NV (US); Mark Santos, Las Vegas, NV (US); Germana Rappa, Las Vegas, NV (US); Patrizia Diana, Palermo (IT); Girolamo Cirrincione, Palermo (IT); TECHNISCHE UNIVERSITÄT DRESDEN, Dresden (DE); BASCK INVEST LTD, Cambridge (GB); Giuseppe Pizzorno, Signal Mountain, TN (US); Andrea Dagnino, Madrid (ES); Ottavio Dagnino, Palermo (IT); Baldassare Renda, Palermo (IT); Gaspare Spedale, Palermo (IT)

(72) Inventors: Aurelio Lorico, Las Vegas, NV (US); Mark Santos, Las Vegas, NV (US); Germana Rappa, Las Vegas, NV (US); Patrizia Diana, Palermo (IT); Girolamo Cirrincione, Palermo (IT); Denis Corbeil, Dresden (DE)

( * ) Notice: Subject to any disclaimer, the term of this patent is extended or adjusted under 35 U.S.C. 154(b) by 746 days.

(21) Appl. No.: 18/044,294

(22) PCT Filed: Sep. 7, 2021

(86) PCT No.: PCT/IB2021/058131

§ 371 (c)(1),
(2) Date: Mar. 7, 2023

(87) PCT Pub. No.: WO2022/049562

PCT Pub. Date: Mar. 10, 2022

(65) Prior Publication Data

US 2023/0321082 A1 Oct. 12, 2023

(30) Foreign Application Priority Data

Sep. 7, 2020 (GB) ..................................... 2014012

(51) Int. Cl.
*A61K 31/4196* (2006.01)
*A61K 31/4245* (2006.01)
*A61K 31/454* (2006.01)
*A61K 31/496* (2006.01)
*A61K 31/5377* (2006.01)

(52) U.S. Cl.
CPC ........ *A61K 31/496* (2013.01); *A61K 31/4196* (2013.01); *A61K 31/4245* (2013.01); *A61K 31/454* (2013.01); *A61K 31/5377* (2013.01)

(58) Field of Classification Search
CPC .......................... C07D 249/08; A61K 31/4196
See application file for complete search history.

(56) References Cited

U.S. PATENT DOCUMENTS

| | | | | |
|---|---|---|---|---|
| 12,527,789 | B2 * | 1/2026 | Lorico | A61K 31/496 |
| 2008/0249151 | A1 | 10/2008 | Sweeney et al. | |
| 2009/0163545 | A1 | 6/2009 | Scott | |
| 2009/0239848 | A1 | 9/2009 | Kumar et al. | |
| 2016/0068515 | A1 * | 3/2016 | Han | C07D 405/14 548/264.6 |

FOREIGN PATENT DOCUMENTS

| | | | | |
|---|---|---|---|---|
| CN | 109771654 | A | 5/2019 | |
| GB | 2575070 | A * | 1/2020 | A61P 31/18 |
| WO | 2006010545 | A1 | 2/2006 | |
| WO | 2006087077 | A2 | 8/2006 | |
| WO | 2012155063 | A1 | 11/2012 | |
| WO | 2018077923 | A1 | 5/2018 | |

OTHER PUBLICATIONS

CAS Registry database: compound 2182410-63-3. Published Mar. 1, 2018 (Year: 2018).*
Examination Report under Section18(3) issued for United Kingdom Patent Application GB2014012.5, on Sep. 9, 2024, 09 Pages.
Oncogene, vol. 37, 2018, Lin et al.,"CIGALTI predicts poor prognosis and is a potential therapeutic target in head and neck cancer", pp. 5780-5793.
Cell Death and Disease, vol. 11, No. 539, 2020, Deng et al., "Itraconazole inhibits the hedgehog signaling pathway thereby inducing autophagy-mediated apoptosis of colon cancer cells", pp. 1-15.
Anticancer Research, vol. 36, 2016, Inoue et al.,"Expression of hedgehog signals and growth inhibition by itraconazole in endometrial cancer", pp. 149-154.
Antiviral Research, vol. 157, 2018, Meutiawati et al.,"Posaconazole inhibits dengue virus replication by targeting oxysterol-binding protein", pp. 68-79.
International Search Report and Written Opinion received for International Patent Application No. PCT/IB2021/058131, dated Dec. 23, 2021, 17 pages.
International Preliminary Report on Patentability received for International Patent Application No. PCT/IB2021/058131 dated Mar. 16, 2023, 12 pages.
Communication Pursuant to Article 94(3) EPC received for European Patent Application No. EP21790552.0 dated Feb. 5, 2025, 10 pages.

(Continued)

*Primary Examiner* — George W Kosturko
(74) *Attorney, Agent, or Firm* — RC Trademark Company

(57) ABSTRACT

There is disclosed a compound selected from triazole analogues or pharmaceutically acceptable salt, hydrate, solvate or prodrug thereof is for use in inhibiting a tripartite VAP-A, ORP3 and Rab7 (VOR) protein complex in multicellular organisms by interfering with at least one mechanism of: intercellular communication, wherein the intercellular communication is mediated by receptor-ligand interaction and/or EVs; and viral infection involving the transport of endocytosed biomaterials to the nucleus of recipient cells.

1 Claim, 25 Drawing Sheets

(56) References Cited

OTHER PUBLICATIONS

Saleem Muhammad, "Synthesis, Crystal Structure, Anti-Inflammatory and Anti-Hyperglycemic Activities of Novel 3, 4-Disubstituted 1,2,4-Triazol-5 (4H)-One Derivatives" Medicinal Chemistry, Jan. 1, 2014, pp. 810-823, XP055870821, vol. 10.

Hall TH et al: "Antinoplastic activities and cytotoxicity of 1-acyl and 1,2-diacyl-1, 2, 4-triazolidine-3, 5-diones in murine and human tissue culture cells", Anticancer Research, International Institute of Anticancer Research, GR, vol. 12, No. 5 Jan. 1, 1992, pp. 1355-1362.

Chunquan Sheng et al: "Design and synthesis of novel triazone antifungal denvatives by structure-based bioisosterism", European Journal of Medicinal Chemistry, Elsevier, Amsterdam, NL, vol. 46, No. 11, Mar. 10, 2011, pp. 5276-5282.

Santos Mark F. et al, "Itraconazole inhibits nuclear delivery of extracellular vesicle cargo by disrupting the entry of late endosomes into the nucleoplasmic reticulum", UK Aug. 1, 2021 (Aug. 1, 2021), vol. 10, No. 10, Retrieved from the Internet: URL:https://onlinelibrary.wiley.com/doi/full-xml/10.1002/jev2.12132 XP055870300, pp. 1-28.

* cited by examiner

FIG. 3A, B

SW480 cells

SW480 cells

SW480 cells

SW480 cells

SW480 cells

SW480 cells

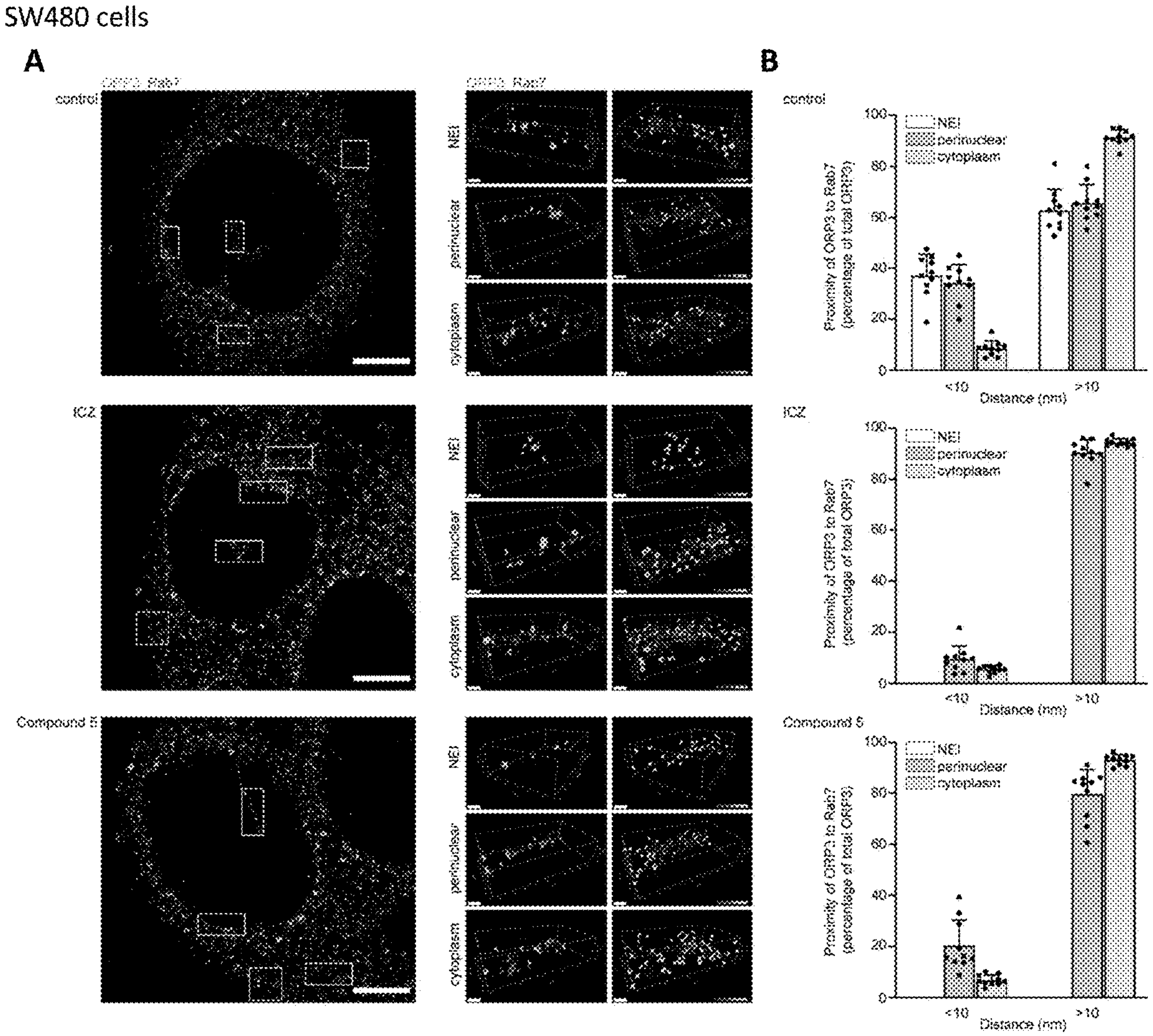
FIG. 13A, B

SW480 cells
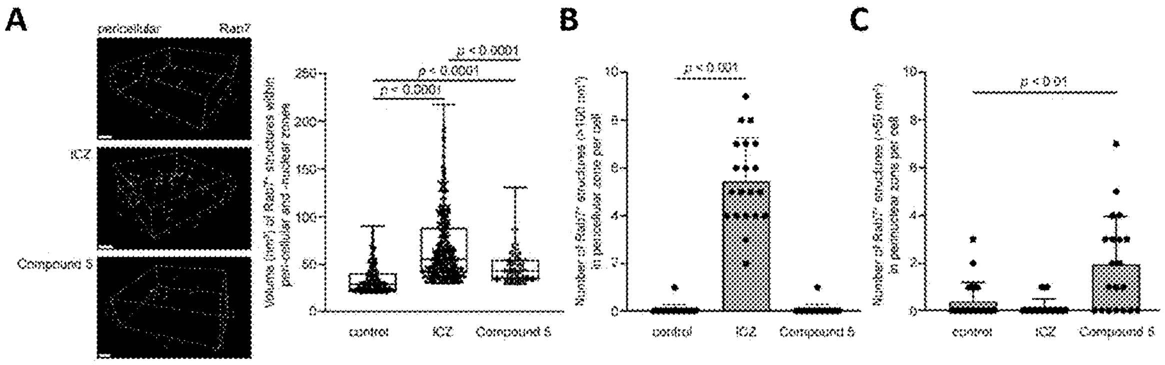
FIG. 14A-C

SW480 cells
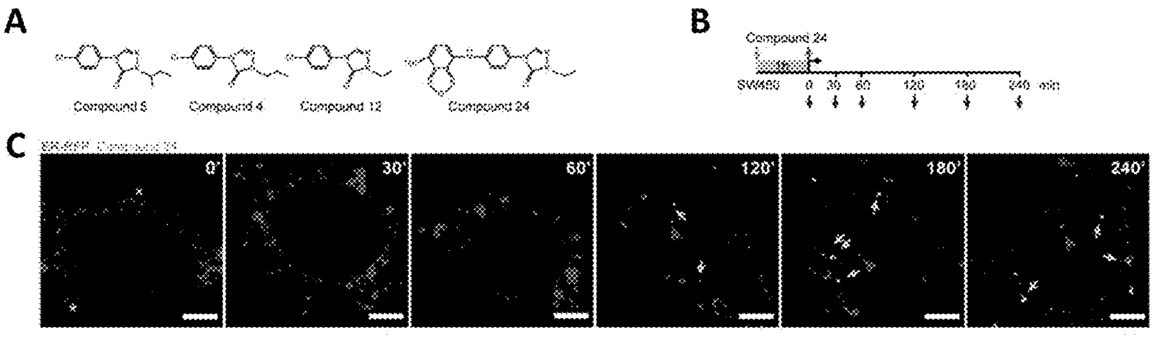
FIG. 15A-C

HeLa cells

HeLa cells

USE OF TRIAZOLE ANALOGUES FOR INHIBITION OF A TRIPARTITE VOR PROTEIN COMPLEX IN MULTICELLULAR ORGANISMS

TECHNICAL FIELD

The present disclosure relates generally to the use of triazole analogues or pharmaceutically acceptable salt, hydrate, solvate or prodrug thereof for the prevention or treatment of cancer and infectious diseases. Specifically, the present disclosure relates to triazole analogues or pharmaceutically acceptable salt, hydrate, solvate or prodrug thereof for use in inhibiting a tripartite VAP-A, ORP3 and Rab7 (VOR) protein complex in multicellular organisms.

BACKGROUND

Cancer and certain viral diseases (such as, HIV-1) are among the leading causes of fatal illness, with millions of deaths due to such diseases worldwide.

Despite the rapid advances in biomedical sciences, the practices employed for the treatment of such fatal diseases are still inadequate in many cases. Traditionally, many immunotherapeutic strategies are being explored to combat cancer, viral infections and age-related diseases. Treatments based on chemotherapy may be employed for curing cancer. One approach is the inhibition of the process of cell multiplication, killing dividing cells by mutilating the control center (namely, nucleus) of such dividing cells or by interrupting the chemical processes involved in cell division.

Antiretroviral (ARV) therapy may be employed for curing viral diseases such as HIV-1. Typically, such ARV therapy employs drugs that target affected cells at different phases of their life cycle. Subsequently, such drugs inhibit cell fusion by preventing the virus from entering or by preventing the copying of viral RNA into DNA and further block the virus from integrating or duplicating. However, these practices have severe limitations such as fluctuations in the molecular composition of the involved cells, challenges in defining the composition of the involved cells, low level of membrane expression of the requisite peptide complexes, presence of immunosuppressive cytokines converting the cells into a tolerogenic state and problems regarding storage and stability management.

Conventionally, antiangiogenic agents are used to treat certain cancers, alone or in combination with traditional cytotoxic drugs. However, tumors are highly adaptable; thus, they may become resistant to such cytotoxic drugs and radiation. Furthermore, in some animal models, these treatments even make the tumors more aggressive, leading to advanced stages of the disease, such as advanced cancer, metastatic cancer and so forth. In other words, responses to such practices (such as, chemotherapy, AVP therapy and so forth) may be transient and may lead to development of drug resistance. Consequently, the effectiveness of such medications in curing the disease decline drastically.

There exists a need to overcome the aforementioned drawbacks associated with the conventional practices for curing diseases such as cancer and viral diseases.

SUMMARY

The present disclosure seeks to provide a therapeutic use of triazole analogues or pharmaceutically acceptable salt, hydrate, solvate or prodrug thereof for treatment of cancer and infectious diseases and any medical disorder mediated by extracellular membrane vesicles (indicated by "EVs" hereafter) or extracellular ligands.

Moreover, the present disclosure provides a triazole analogue or pharmaceutically acceptable salt, hydrate, solvate or prodrug thereof for inhibiting a tripartite protein complex composed by vesicle-associated membrane protein (VAMP)-associated protein A (VAP-A), oxysterol-binding protein (OSBP)-related protein-3 (ORP3) and small GTPase Rab7 (VOR) in multicellular organisms for the treatment of cancer and infectious diseases and any medical disorder mediated by EVs or extracellular ligands.

In a first aspect, embodiments of the present disclosure relate to a compound selected from triazole analogues or pharmaceutically acceptable salt, hydrate, solvate or prodrug thereof is for use in inhibiting a tripartite VAP-A, ORP3 and Rab7 (VOR) protein complex in multicellular organisms by interfering with at least one mechanism of:

(a) intercellular communication, wherein the intercellular communication is mediated by receptor-ligand interaction and/or EVs; and (b) viral infection involving the transport of endocytosed biomaterials to the nucleus of recipient cells.

An advantage of the present invention is the provision of an orally administrable compound for the inhibition of a tripartite VOR protein complex in the treatment of cancer, infectious diseases and any medical disorder mediated by EVs or extracellular ligands.

Optionally, the triazole analogues has the following structure:

Formula I

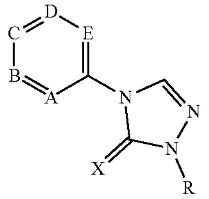

wherein,

A, B, C, D, E are each independently selected from $CR^1$ or N;

R is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, haloalkyl, haloalkenyl, haloalkynylalkyl, haloalkoxy heteroalkyl, heterocycloalkyl, heteroaryl, heteroarylalkyl, heterocycloalkylalkyl, alkylsulfonyl and any optical substitutes thereof; and X is selected from O, S and $CH_2$.

More optionally, the $R^1$ is selected from the group consisting of hydrogen, alkyl, arylalkyl, alkoxyalkyl, arylalkoxy, alkynylalkyl, alkylalkynylalkyl, alkenylalkyl, alkylalkenylalkyl, amino, amido, cycloalkyl, cyanoalkyl, cycloalkylalkyl, halogen, haloalkyl, haloalkenyl, haloalkynylalkyl, haloalkoxy, nitro and any optical substitutes thereof.

Optionally, the triazole analogues has the following structure of Formula II or an optically pure stereoisomer or pharmaceutically acceptable salt, hydrate, solvate or prodrug thereof:

Formula II

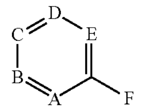

wherein,

A, B, C, D, E are each independently selected from $CR^1$ or N; and $R^1$ is selected from the group consisting of hydrogen, alkyl, arylalkyl, alkoxyalkyl, arylalkoxy, alkynylalkyl, alkylalkynylalkyl, alkenylalkyl, alkylalkenylalkyl, amino, amido, cycloalkyl, cyanoalkyl, cycloalkylalkyl, halogen, haloalkyl, haloalkenyl, haloalkynylalkyl, haloalkoxy, nitro and any optical substitutes thereof.

Optionally, the F is selected from the group consisting of:

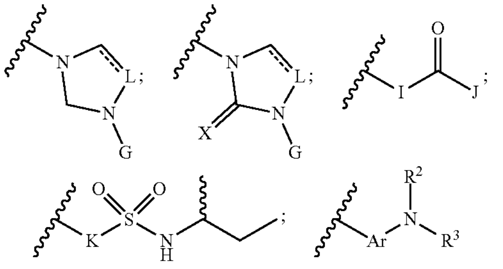

wherein, is a single or a double bond.

Optionally, the L is selected from $CH_2$, CH and NH.

Optionally, the G is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, haloalkyl, haloalkenyl, haloalkynylalkyl, haloalkoxy heteroalkyl, heterocycloalkyl, heteroaryl, heteroarylalkyl, heterocycloalkylalkyl, alkylsulfonyl and any optical substitutes thereof.

Optionally, the X is selected from O, S and $CH_2$.

Optionally, the I is selected from $(CH_2)_mCH_3$ and $NR^4$.

Optionally, the J is $(CH_2)_nCH_3$ and $NR^5R^6$.

Optionally, the $R^4$ is selected from H, unsubstituted C1-6 alkyl and substituted C1-6 alkyl.

Optionally, the $R^5$ is selected from H, unsubstituted C1-6 alkyl, substituted C1-6 alkyl.

Optionally, the $R^4$ and $R^5$ are joined to form an unsubstituted or substituted 5- or 6-membered ring with the —N-(=J)-N— moiety, wherein the $R^4$ and $R^5$ form an unsubstituted or substituted $C_{2-3}$ carbohydryl group or an unsubstituted or substituted $C_{1-2}$ carbohydryl group linked via a nitrogen to a nitrogen of the —N-(=J)-N— moiety.

Optionally, the $R^6$ is selected from H, substituted or unsubstituted $C_{1-6}$ alkyl, $C_{1-6}$ alkoxy, $C_{2-6}$ alkanoyl, $C_{1-6}$ alkoxcarbonyl, and $C_{1-6}$ haloalkyl.

Optionally, the K is selected from $(CH_2)_p$ and NH.

Optionally, the n, m, p are independent integers between 0 to 4.

Optionally, the Ar is selected from unsubstituted aryl and substituted aryl.

Optionally, the $R^3$ is selected from —C(═O)—$R^7$, —C(═O)—O—$R^7$, and —S(═O)$_n$—$R^7$, wherein the n ranges between 0 to 3, and wherein the $R^7$ is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, heteroalkyl, heterocycloalkyl, heteroaryl, heteroarylalkyl, heterocycloalkylalkyl, alkylsulfonyl, and any optical substitutes thereof.

Optionally, the $R^2$ and $R^3$ along with the nitrogen atom form a nitro ($NO_2$) group.

Optionally, the $R^2$ and $R^3$ are joined to from an unsubstituted or substituted 5- or 6-membered ring with the proviso excluding a —N—(═Z)—N— moiety, wherein the Z is selected from O and S.

Optionally, the compound is used in treatment of at least one of: a condition in which the tripartite VOR protein complex is implicated, a cancer, a cancer metastasis, infectious disease, viral disease, a neurodegenerative disease, a ventricular hypertrophy, a type I diabetes, a type II diabetes, a retinal degeneration including macular degeneration, a lung disease and any other disease where EVs have a pathogenetic role.

Optionally, the cancer includes at least one of: a kidney carcinoma, a bladder carcinoma, an endometrial carcinoma, head and neck cancer or any other type of cancer that expresses ORP3.

Optionally, the viral disease is HIV-1 or any other virus that requires entry of itself or of some of its components or accessory molecules into the nucleus.

According to the invention, triazole analogues or pharmaceutically acceptable salt, hydrate, solvate or prodrug thereof are for use in the treatment or prevention of a disease or condition in which the tripartite VOR protein complex is implicated. They include the nuclear transport of EVs and viruses and/or their cargo contents, viral pre-integration complexes, endocytosed ligands, receptors or ligand-receptor complexes occurring through the VOR complex, which are targeted by the present disclosure.

Beneficially, the present disclosure provides a therapeutic compound that targets intercellular communications, for example, the intercellular communication between a tumor and its host in the case of cancer or between cancer cells themselves within the host. It can also interfere between healthy cells and pathological ones in diseases such as retinal degeneration, diabetes and neurodegenerative diseases, notably those involving EVs and ligand-cell surface receptors. Typically, disruption of such intercellular communications between cell(s) affected by a disease and host(s) of the disease may be a powerful and fruitful strategy to combat the disease. Furthermore, since intercellular communications are implicated in a plurality of other diseases, these disruptions thereby enable effective therapy of a plurality of other diseases.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

A better understanding of the present invention may be obtained through the following examples which are set forth to illustrate but are not to be construed as limiting the present invention.

BRIEF DESCRIPTION OF DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein.

Moreover, those in the art will understand that the drawings are not to scale. Wherever possible, like elements have been indicated by identical numbers.

Figure 1A:
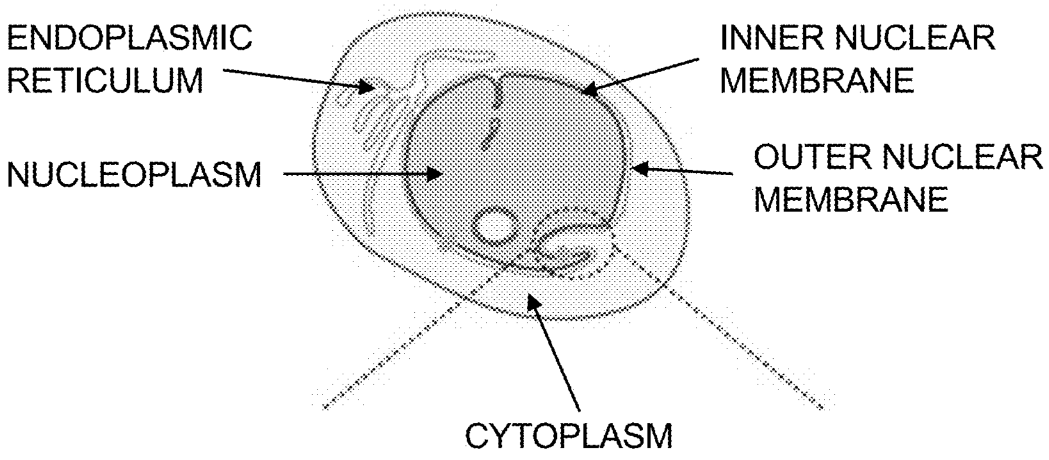
Figure 1B:
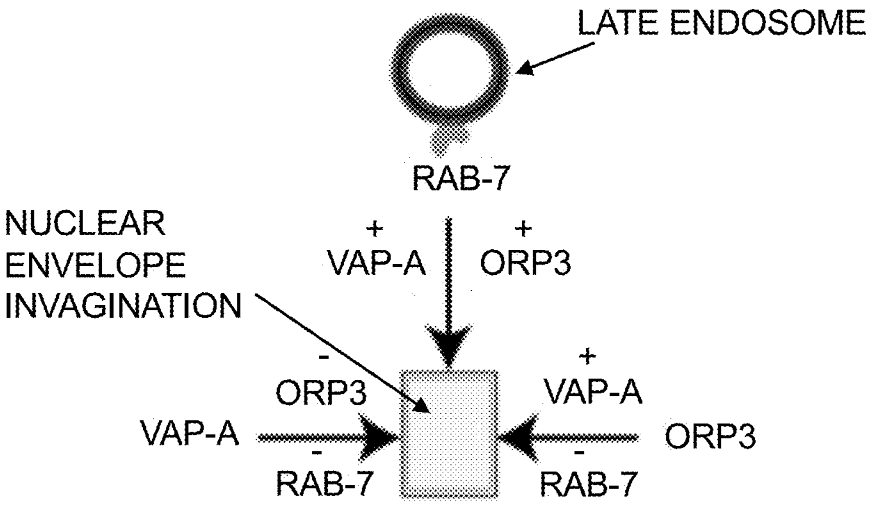
Figure 1C:
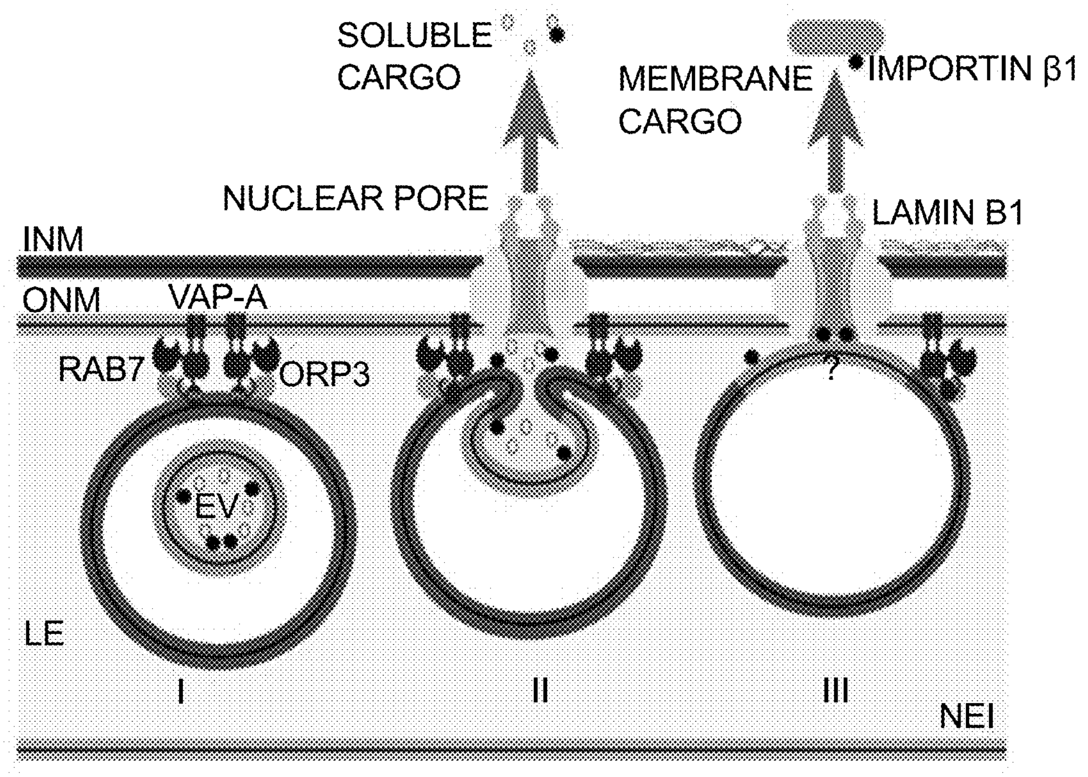
Figure 2:
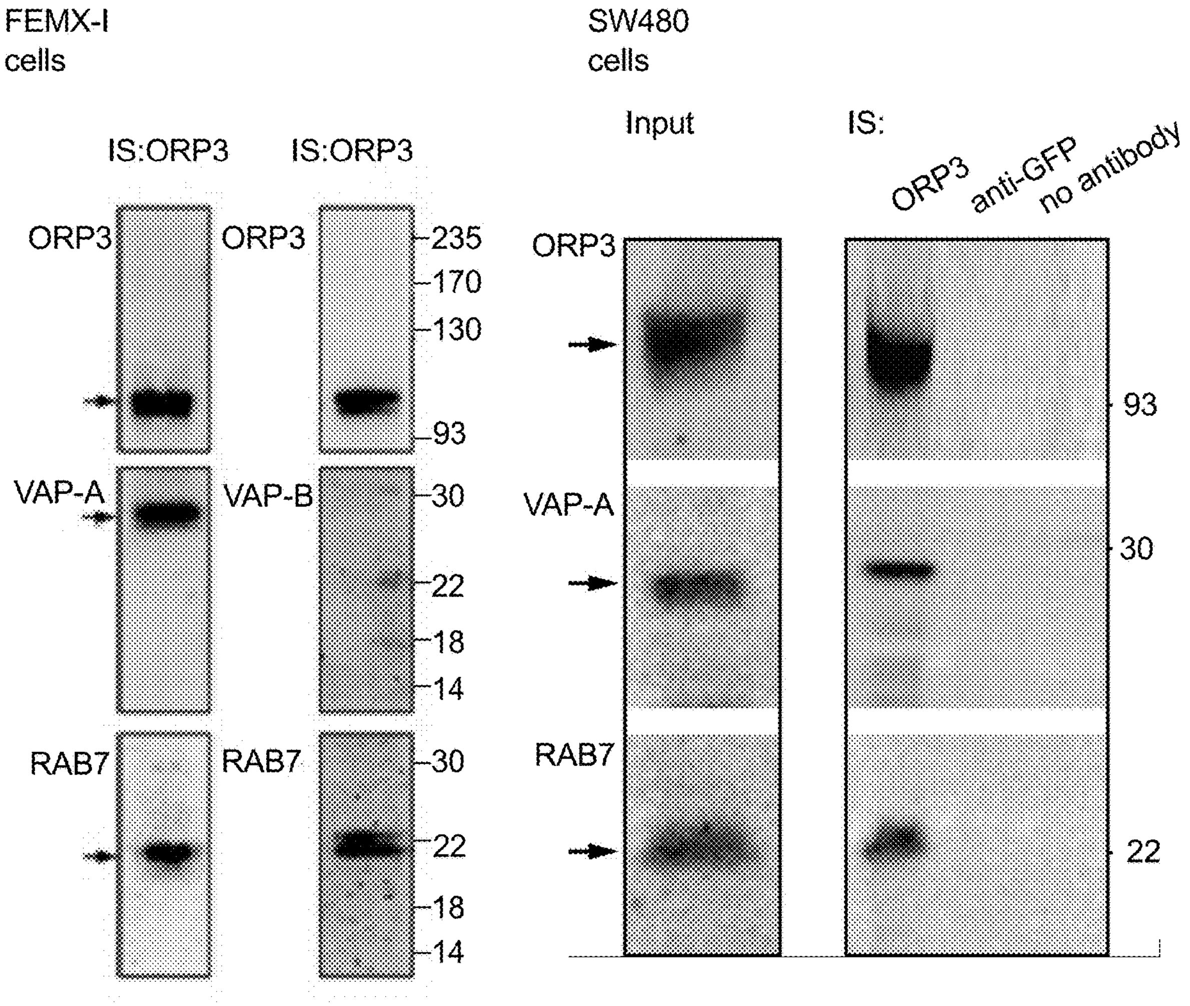
Figure 3:
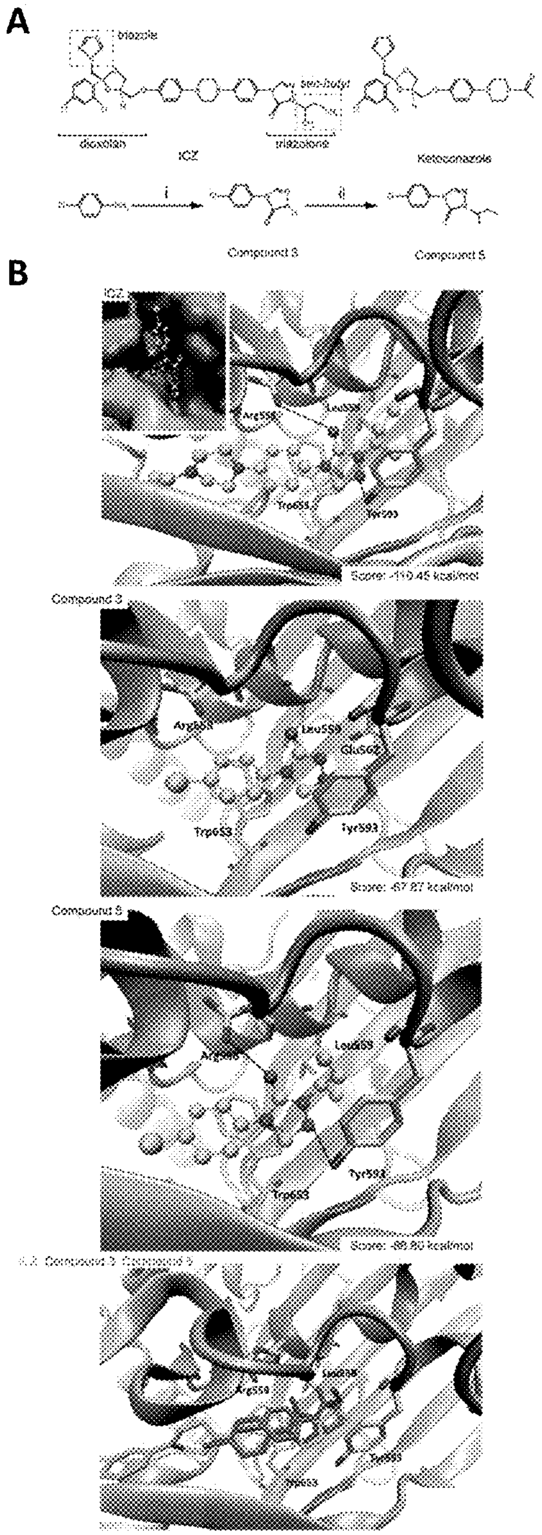
Figure 4:
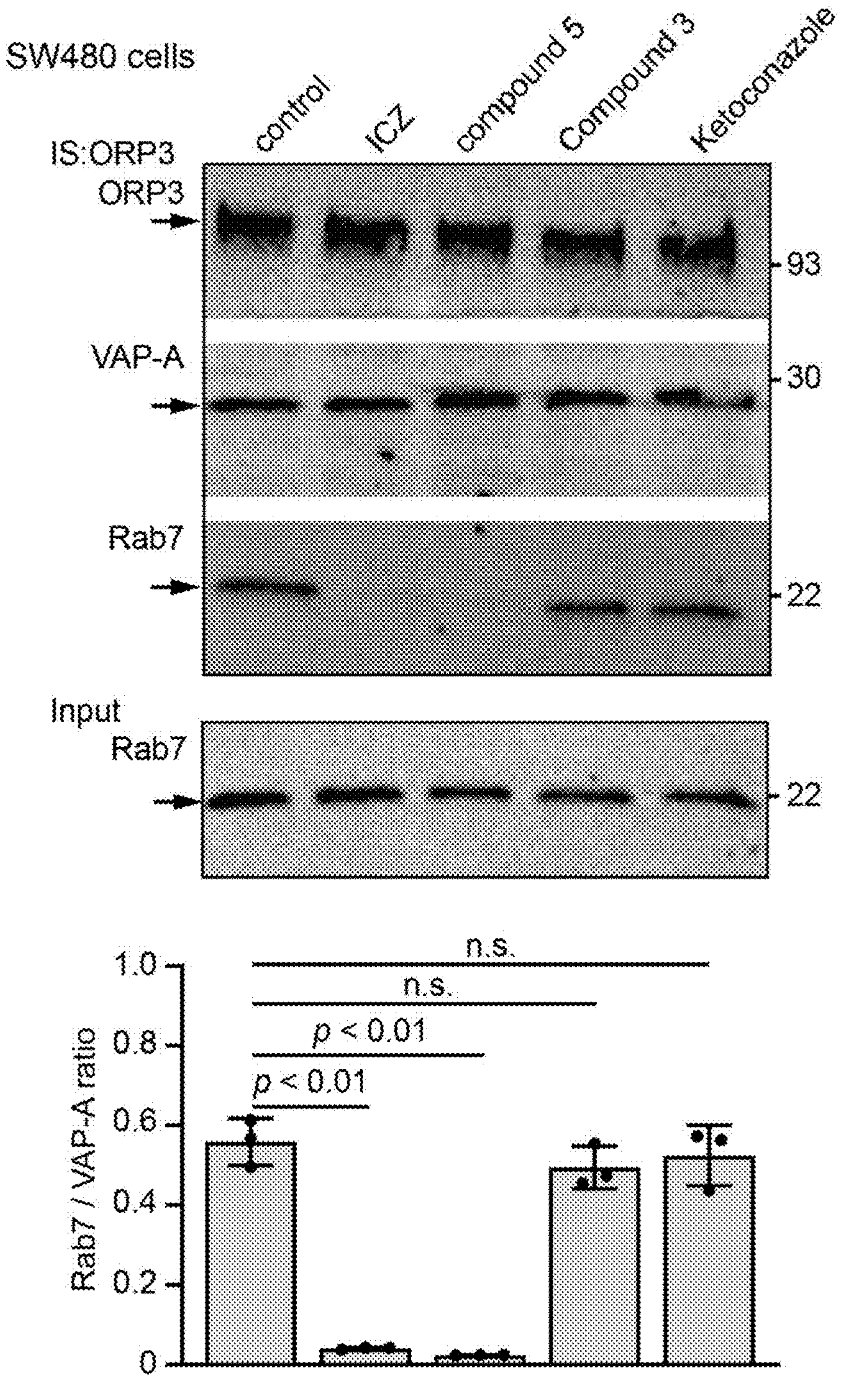
Figure 5:
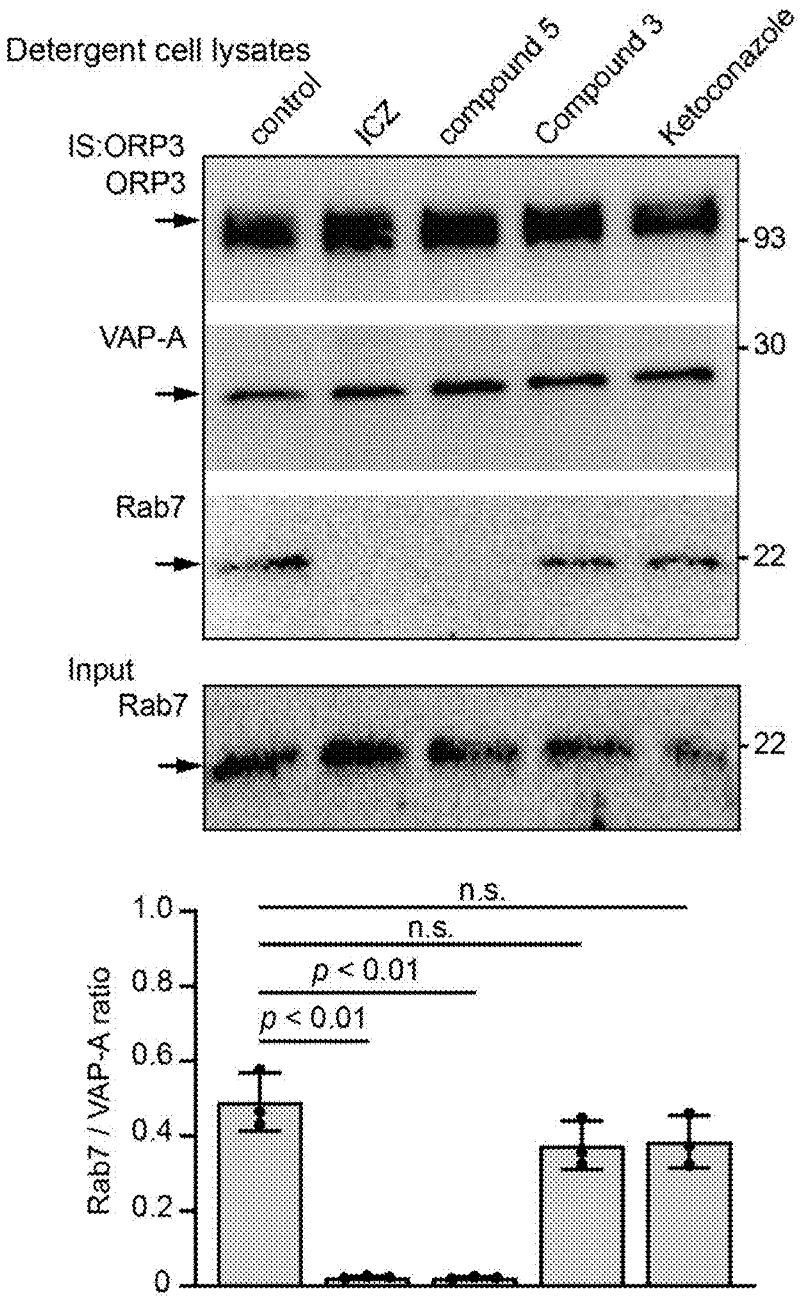
Figure 6:
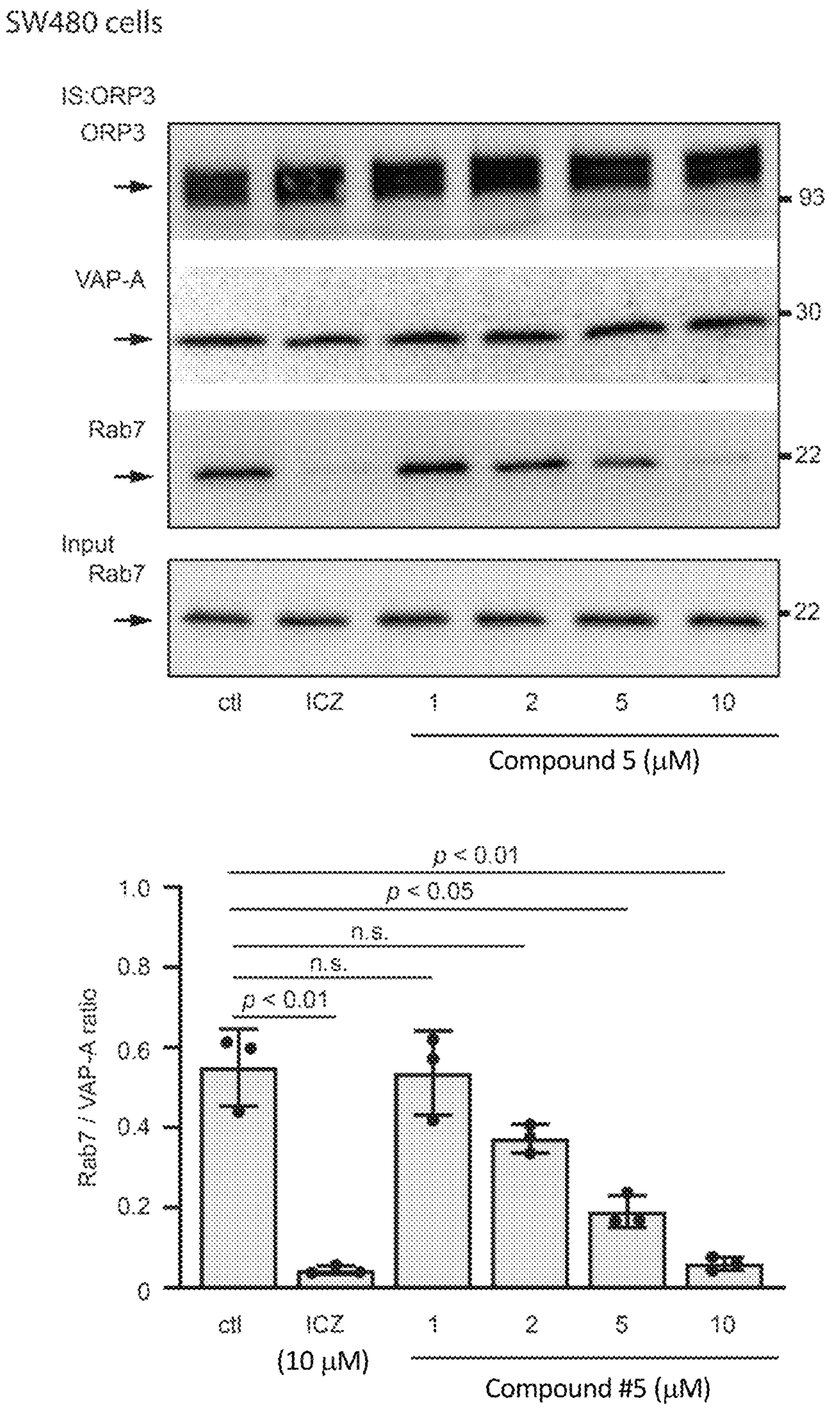
Figure 7:
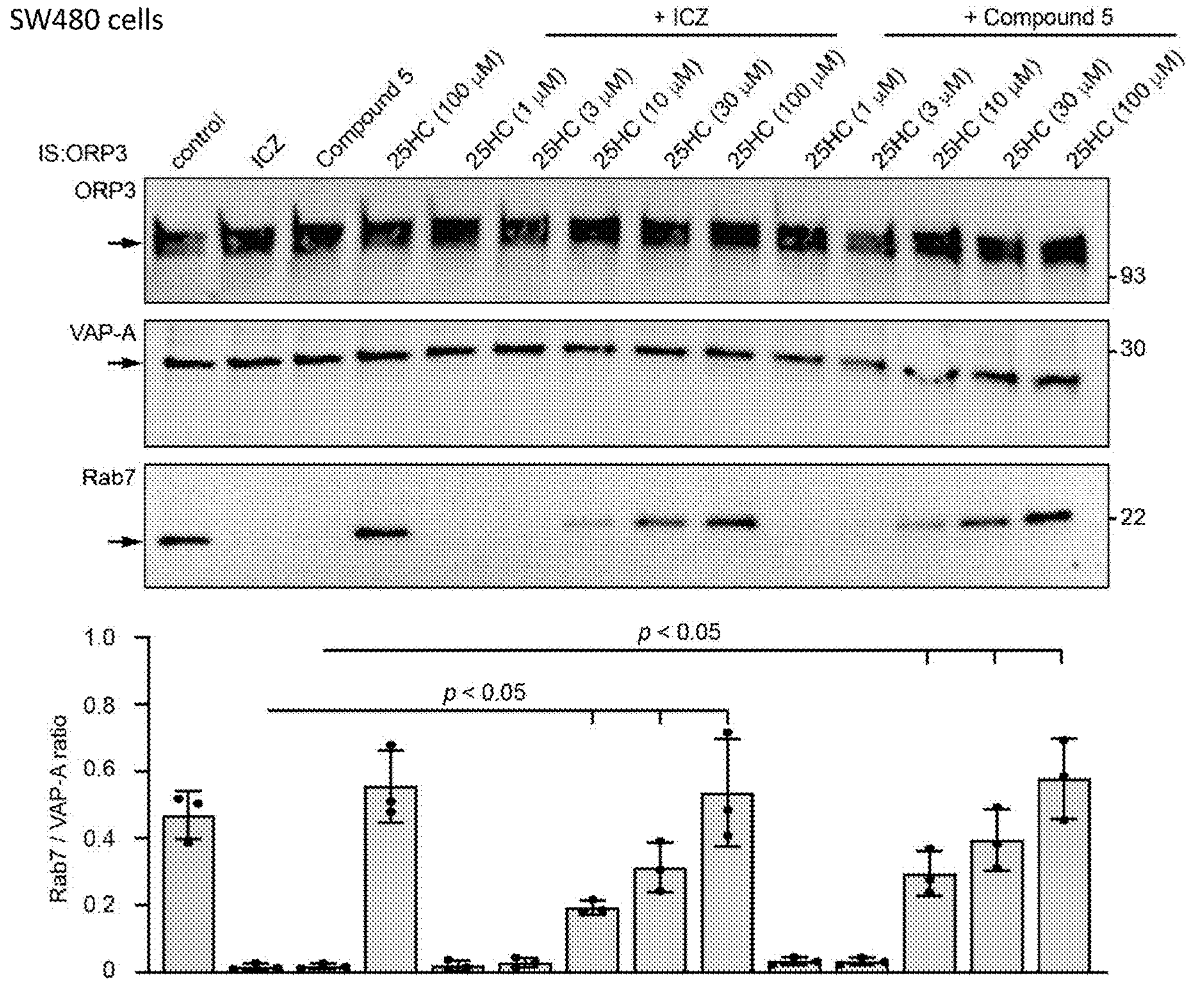
Figure 8:
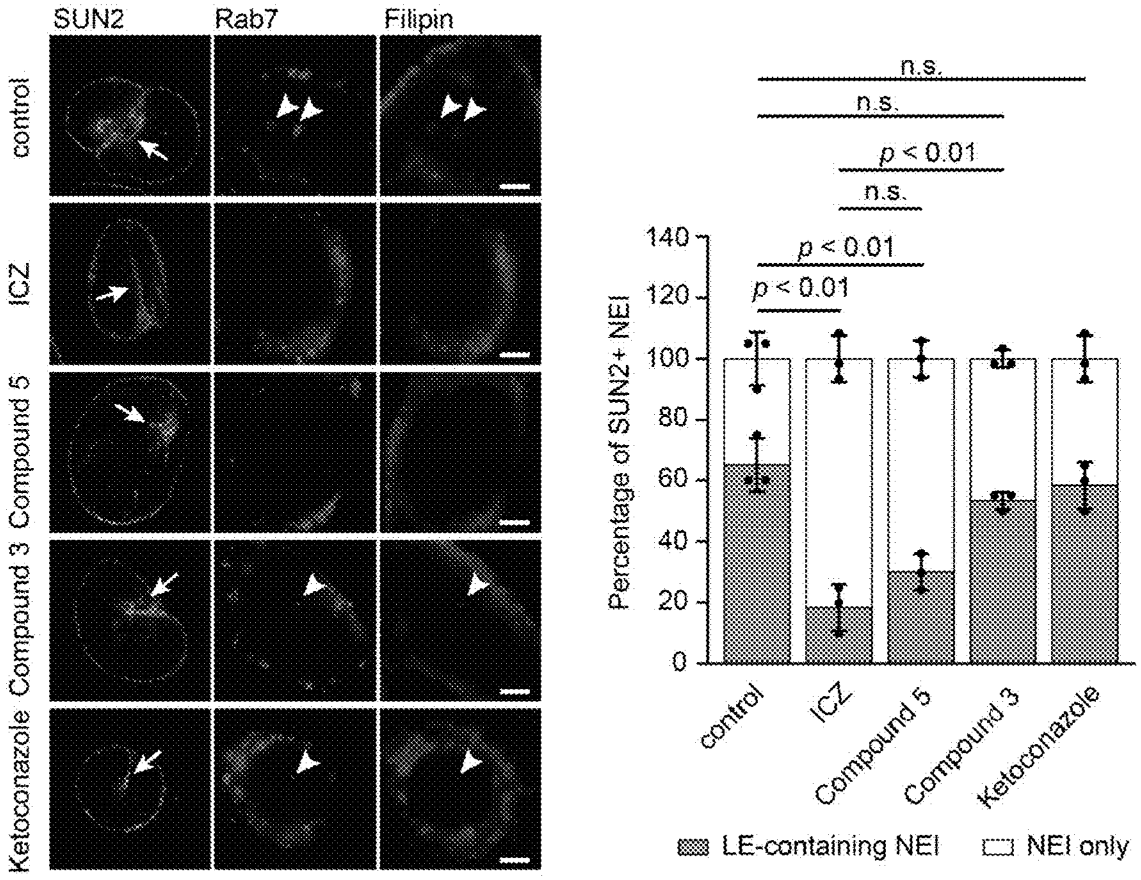
Figure 9:
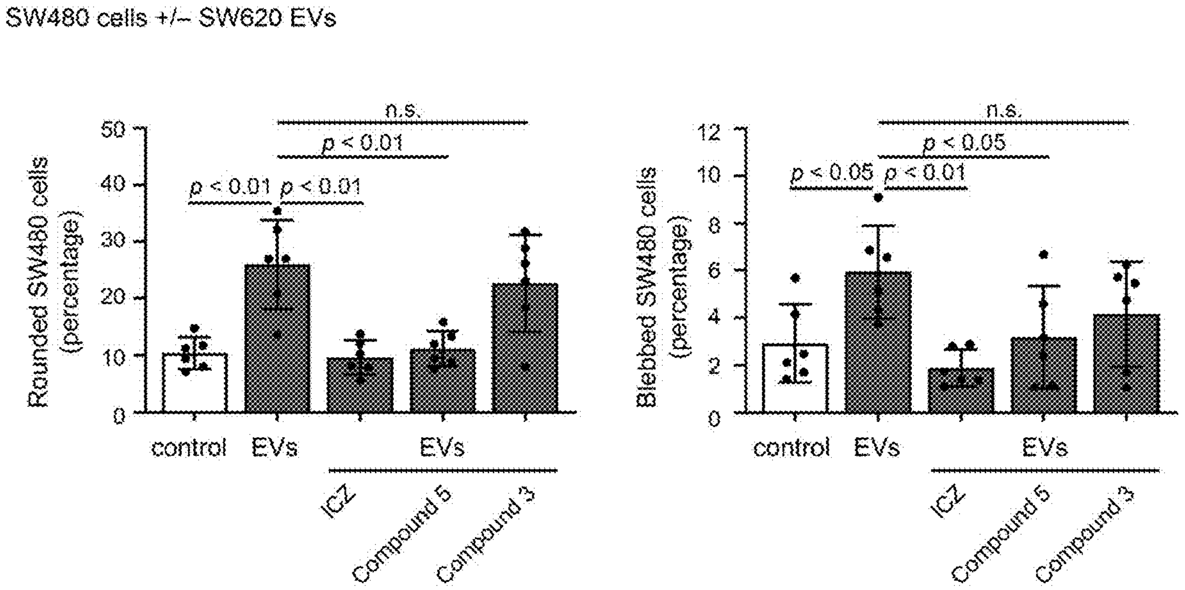
Figure 10:
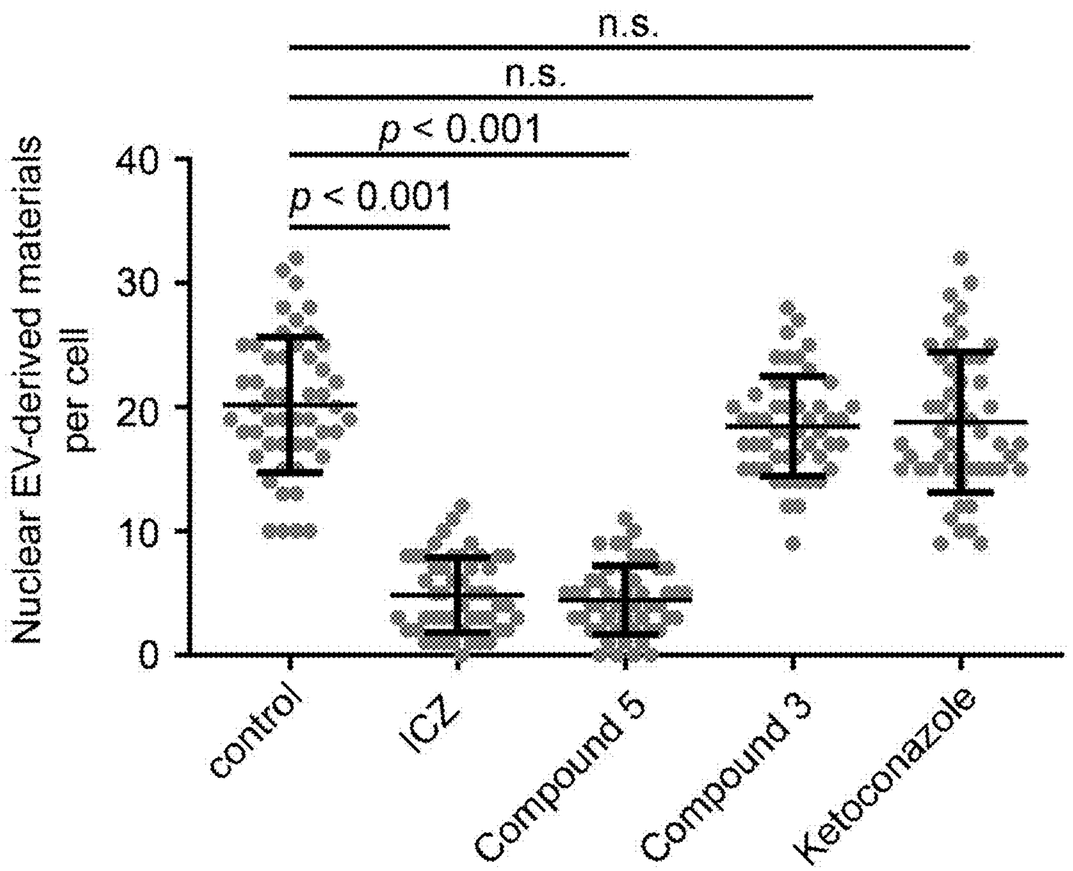
Figure 11:
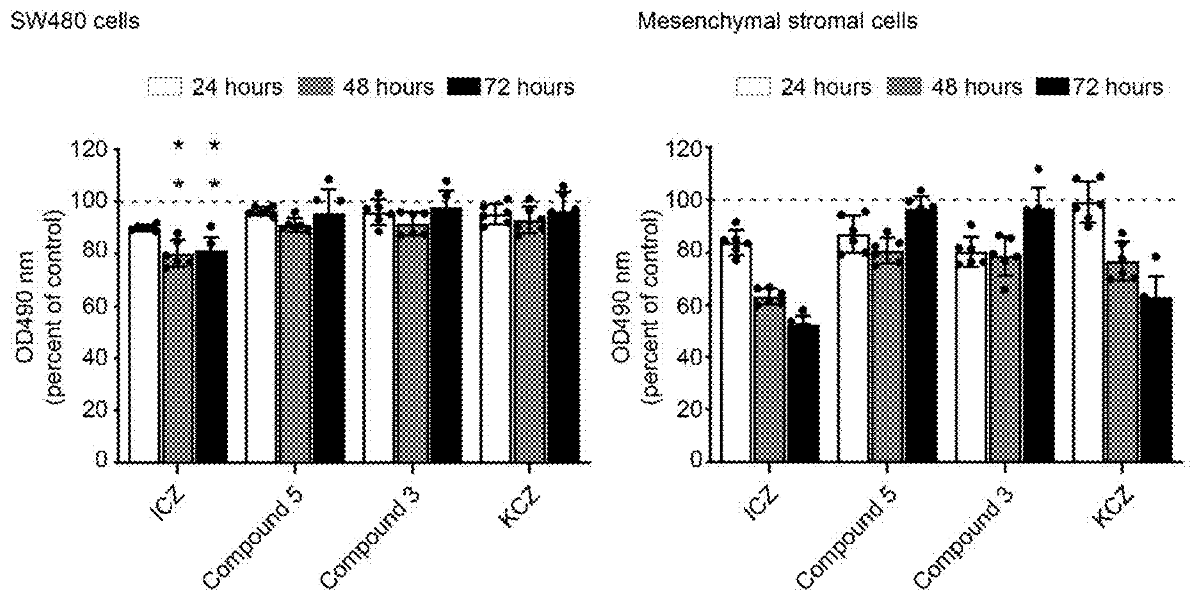
Figure 12A:
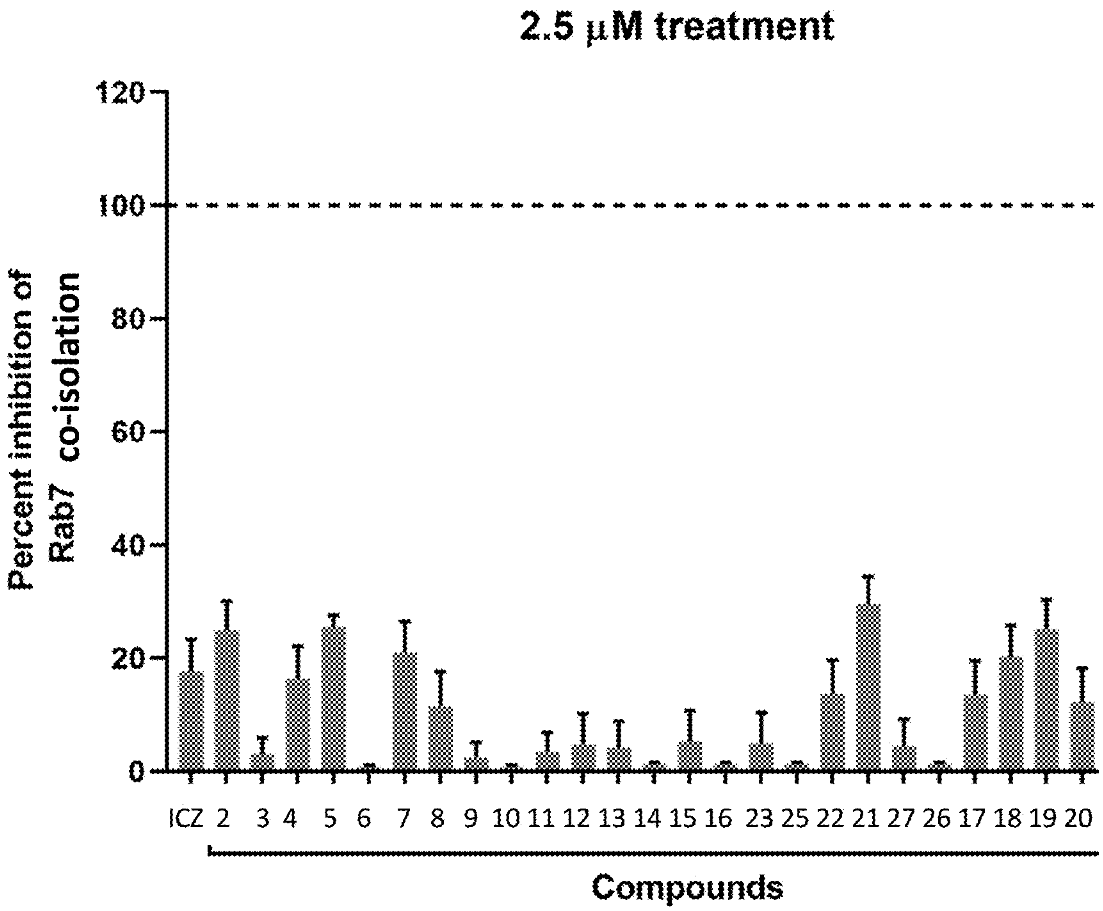
Figure 12B:
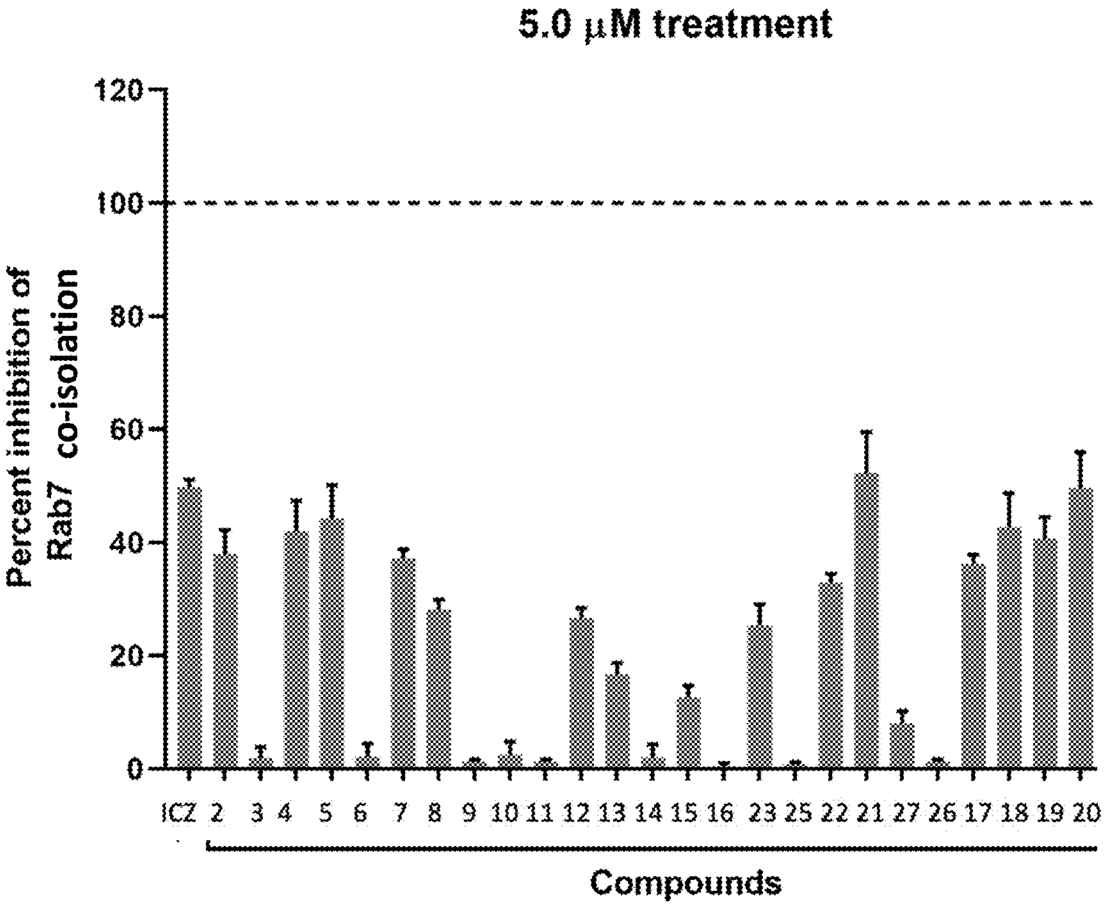
Figure 12C:
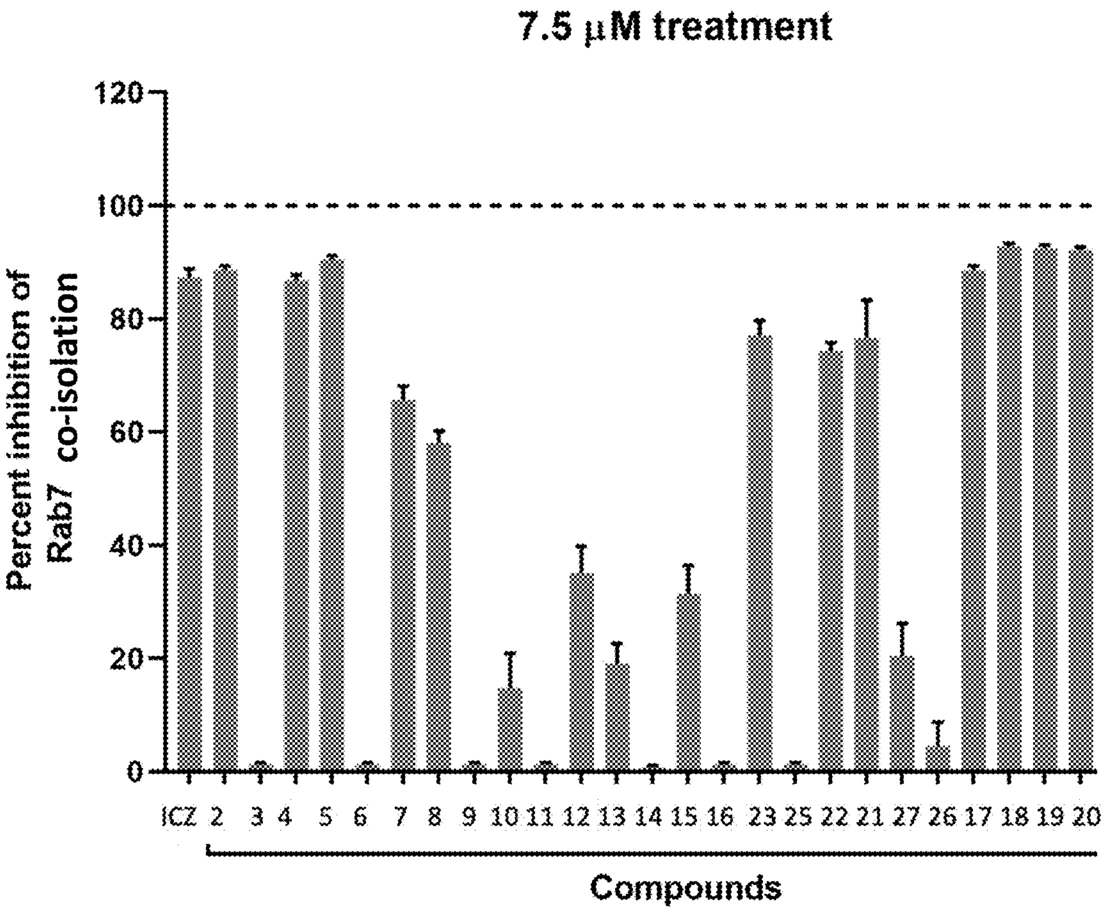
Figure 12D:
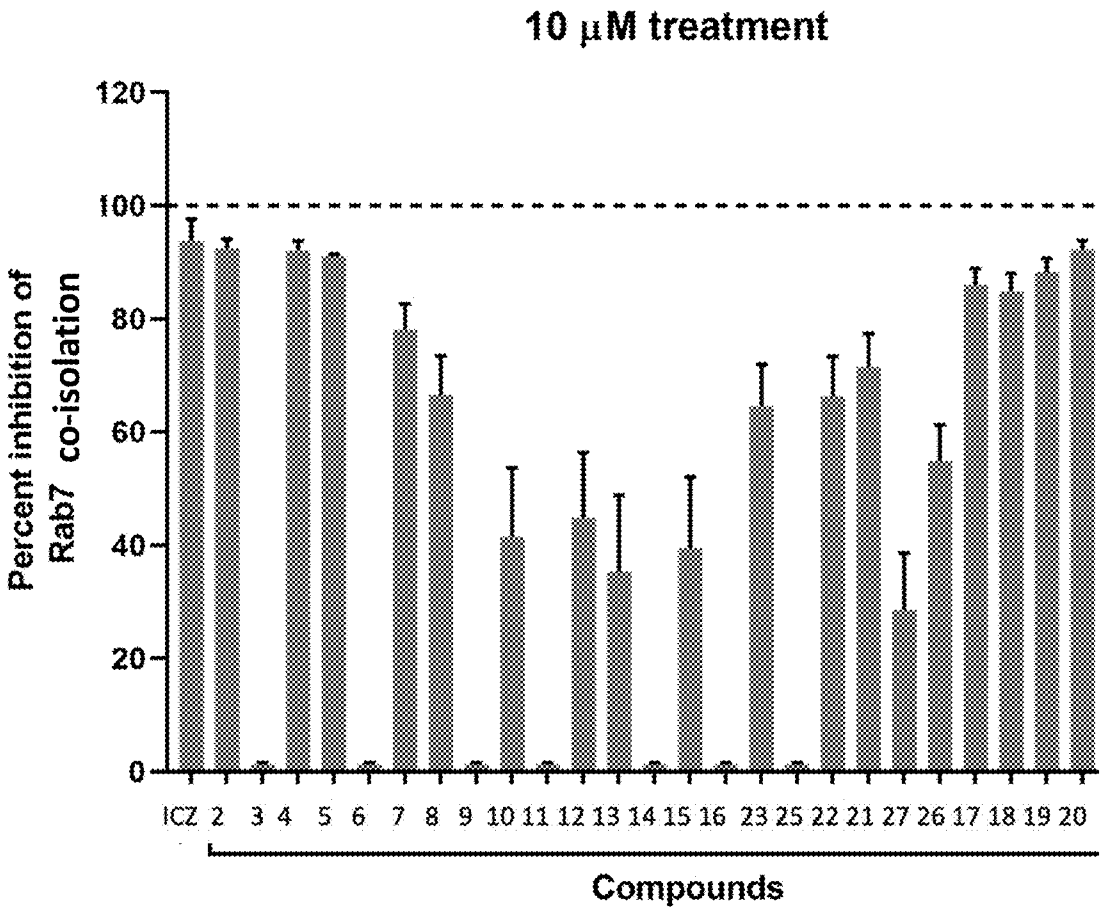
Figure 16:
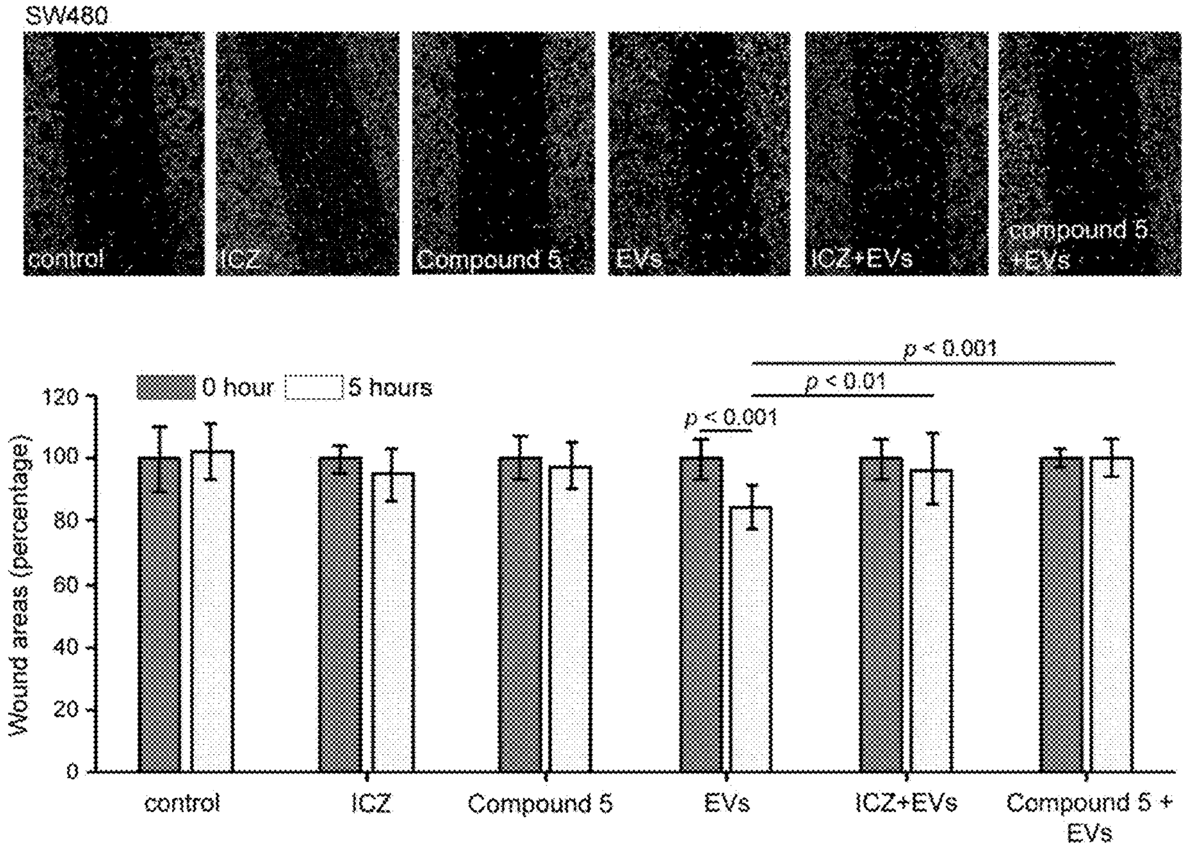
Figure 17:
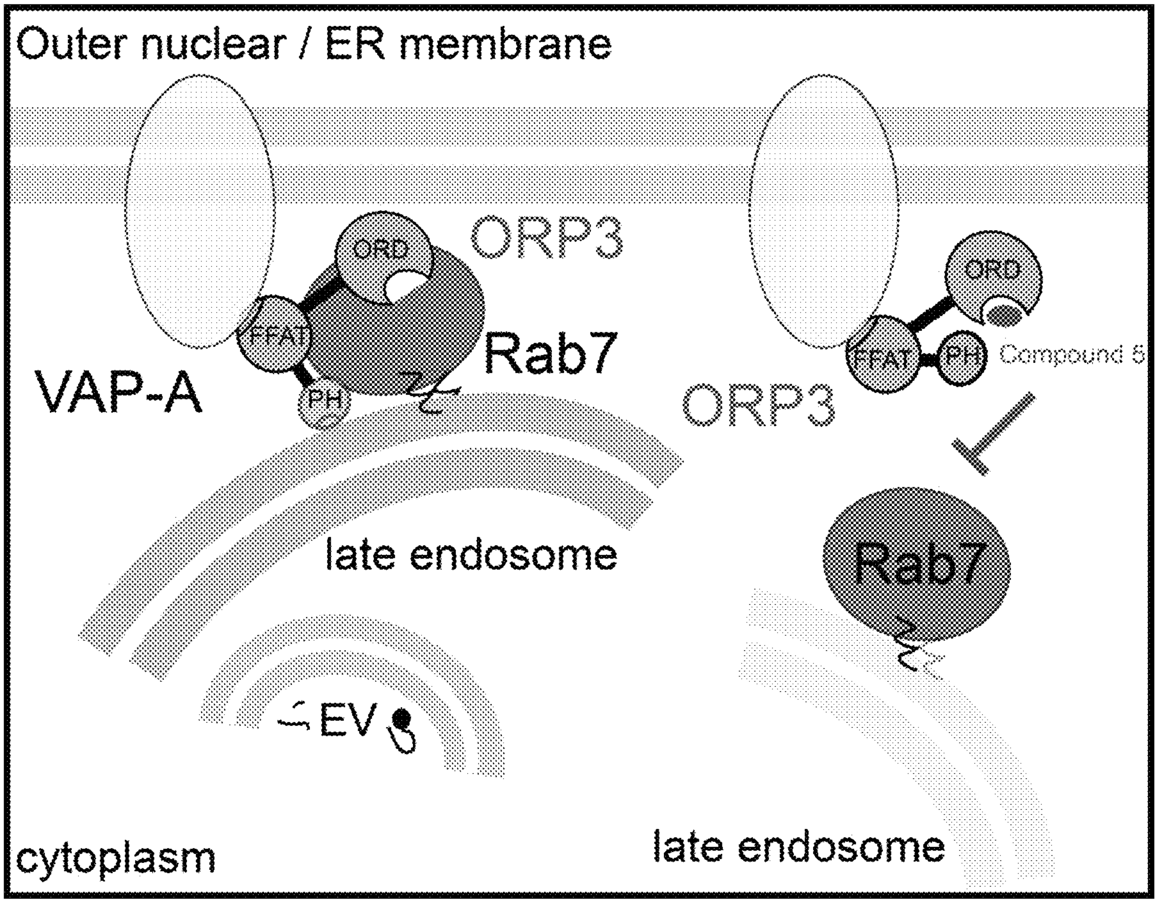
Figure 18:
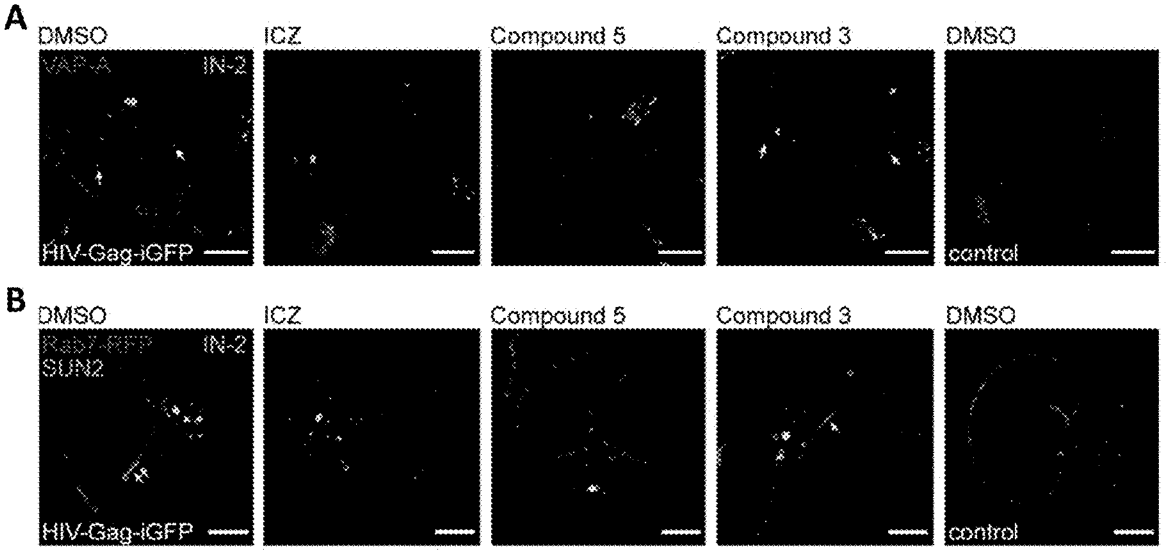
Figure 19:
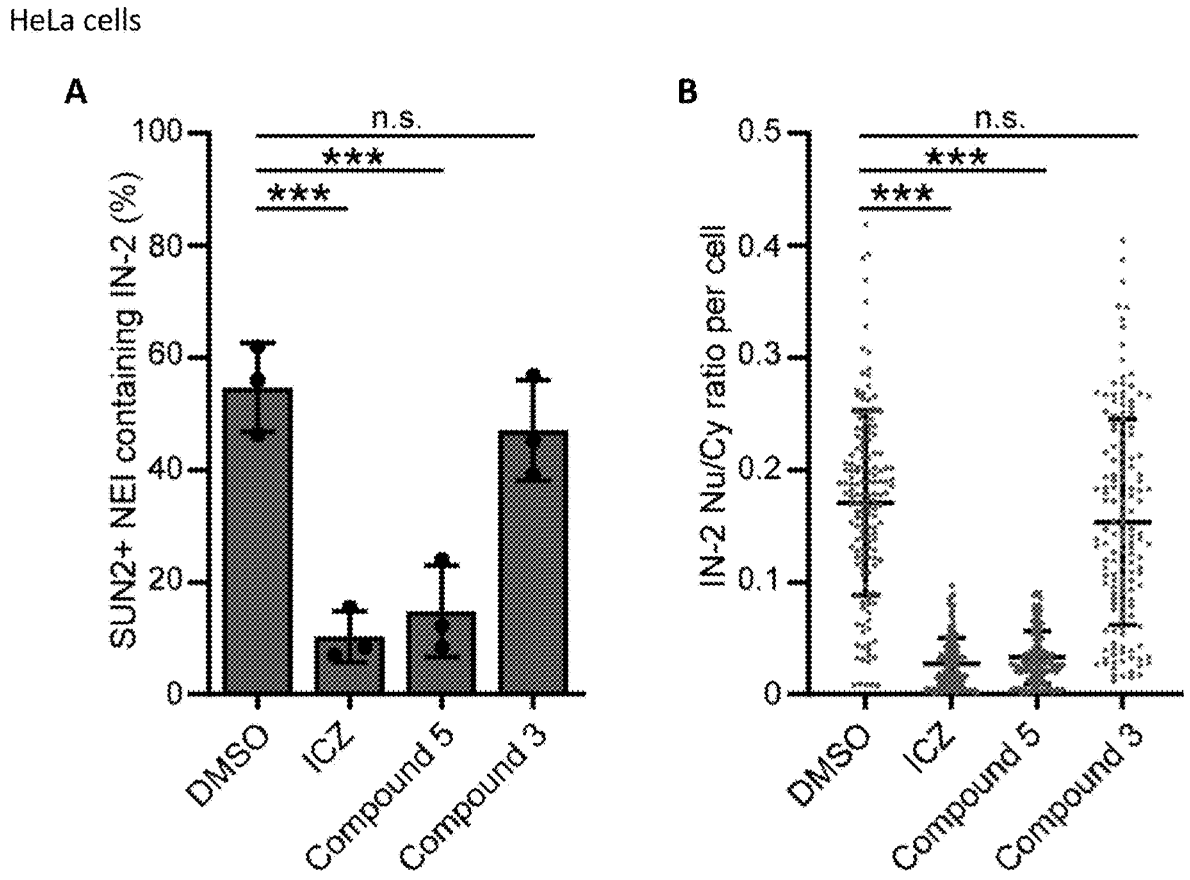
Figure 20:
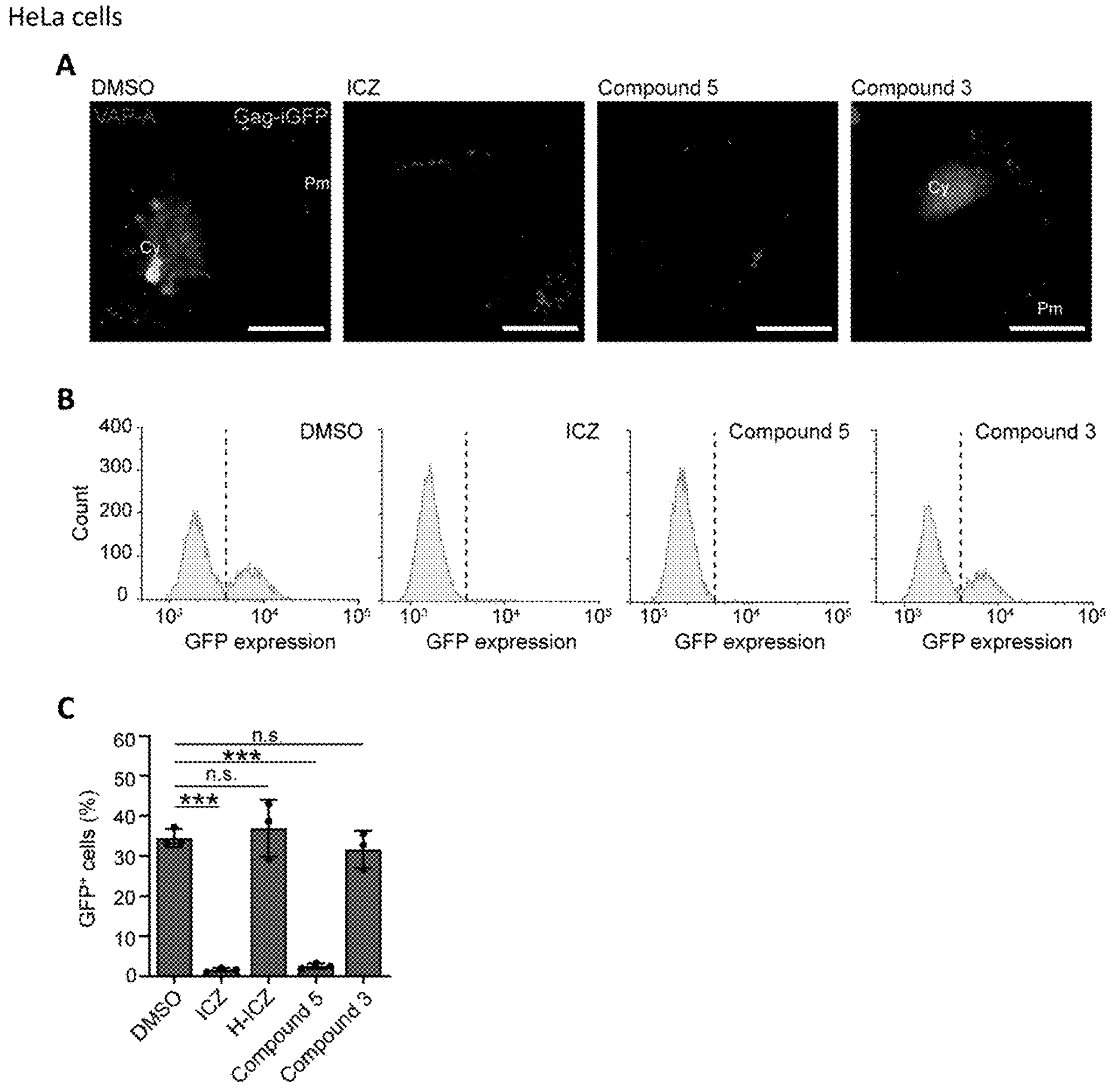
Figure 21:
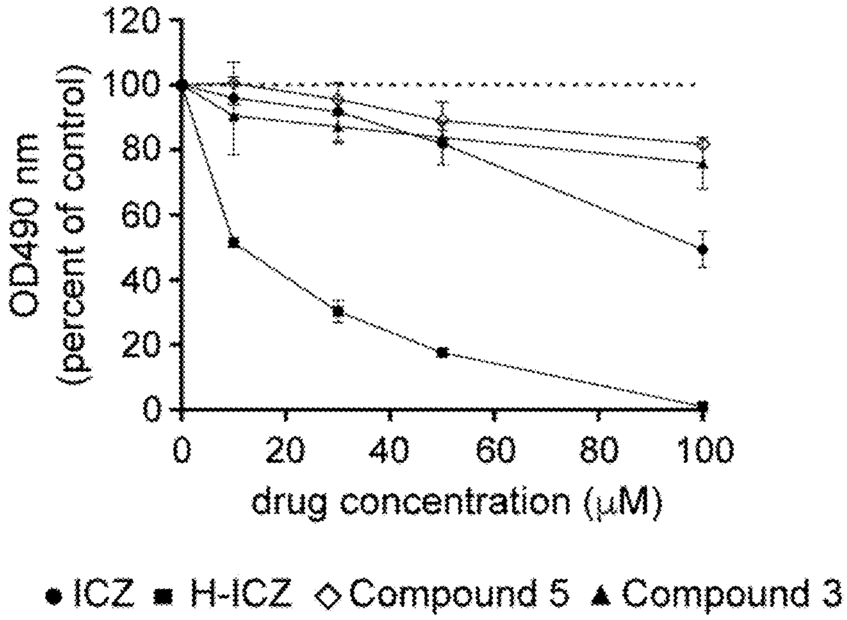

Embodiments of the present disclosure will now be described, by way of example only, with reference to the following diagrams wherein:

FIGS. 1A, 1B and 1C, illustrate data showing the localization and the tripartite structure of a VOR complex (VAP-A, ORP3 and Rab7) and its function in a nuclear envelope invagination (NEI);

FIG. 2 illustrates in two cancer cell lines that upon immunoisolation of ORP3, VAP-A and Rab7 are co-isolated;

FIGS. 3A and 3B, illustrates the synthetic scheme of triazole compounds 3 and 5 and the molecular modelling of ICZ, compound 3 and compound 5 in the conserved C-terminal OSBP-related domain (ORD) pocket of ORP3;

FIG. 4, illustrates the impact of the triazole compound 5, but not compound 3, on the VOR complex integrity in whole cells;

FIG. 5, illustrates the impact of the triazole compound 5, but not compound 3, on the VOR complex integrity in cell lysates;

FIG. 6, illustrates the effects of increasing concentration of triazole compound 5 on the VOR complex integrity;

FIG. 7, illustrates the competition between the 25-hydroxycholesterol and triazole compound 5 to bind the hydrophobic pocket of the ORD of ORP3;

FIG. 8, illustrates that the triazole compound 5 inhibited the entry of $Rab7^+$ late endosomes in NEI;

FIG. 9, illustrates that the triazole compound 5 inhibited EV-induced pro-metastatic morphological transformation;

FIG. 10, illustrates that the triazole compound 5 inhibited the nuclear transfer of EV cargo;

FIG. 11, illustrates that triazole analogues 3 and 5 were not toxic for cells;

FIGS. 12A, 12B, 12C and 12D, illustrates the inhibition of ORP3 by triazole compound 5 and other compounds measured as inhibition of Rab7 binding;

FIGS. 13A and 13B, illustrates the impact of ICZ and compound 5 on the proximity of ORP3 and Rab7 in various subcellular zones;

FIGS. 14A, 14B and 14C, illustrates the 3D-rendered images from pericellular zone were reconstructed to illustrate the difference in volume of $Rab7^+$ structures of control compared with ICZ- and compound 5-treated cells;

FIGS. 15A, 15B and 15C, illustrates the chemical structures of compounds including the fluorescent compound 24, the methodology of the compound 24 experiments and the accumulation of compound 29 in perinuclear space and NEI;

FIG. 16, illustrates that ICZ and compound 5 inhibit the migration of SW480 cells induced by EVs;

FIG. 17, illustrates the inhibition of ORP3 by triazole compound 5;

FIGS. 18A and 18B, illustrates ICZ and compound 5 that inhibit the transport of HIV-1 integrase into the nucleoplasmic reticulum;

FIGS. 19A and 19B, illustrates the quantification of IN-2 immunoreactivity in NEI and the IN-2 nucleoplasm/cytoplasm ratio per cell on HeLa cells treated with ICZ, compound 3 and compound 5;

FIGS. 20A, 20B and 20C, illustrates the impact of drugs on HIV-1 productive infection; and FIG. 21, illustrates the drug toxicity on HeLa cells.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or putting in practice the present disclosure are also possible.

Throughout the present disclosure, the term "multicellular organism" used herein relates to organisms (eukaryotic) with more than one cell, such as humans, animals, plants, fungi, algae and the like. The multicellular organisms are much larger and complex as compared to the unicellular organisms (with only one cell). Due to various cells, the multicellular organisms have a competitive advantage in terms of lifespan, growth, specialization, division of labor, efficiency and so forth. The functional aspects of the multicellular organisms often require the cells to be independent yet integrated to varying degrees. In other words, the multicellular organisms grow in size and number (or reproduce), metabolize nutrients and react to stimuli to perform efficiently in one or more processes of life. Nonetheless, various cells are dependent on each other and interact to perform specialized functions.

Specifically, the cells interact with each other through intercellular communication. The intercellular communication relates to communication between two or more cells. It may be appreciated that during the course of evolution, the multicellular organisms have developed various intercellular communication strategies, including but not limited to cell-cell contact, soluble molecules, quorum sensing, EVs, and so forth. Furthermore, the intercellular communication enables reception, transduction and response generation in the presence of stimuli, such as a water soluble signaling molecule, an antigen, a chemical substance and so forth. Nonetheless, it will be appreciated that intercellular communications expose the multicellular organisms to a higher risk of cancer or pathogenesis.

As mentioned previously, the intercellular communication is mediated by various means and are well-known to a person skilled in the art. Optionally, the intercellular communication is carried out by release of an intercellular communication messenger by cells of the recipient cell population. Specifically, the intercellular communication messenger of one recipient cell population interact with the cells of another recipient cell population to mediate the cell-cell interaction or the intercellular communication. The intercellular communication messengers include, but are not limited to, growth factors, cytokines (such as interleukins (IL), interferons (IFNs), tumor necrosis factors (TNFs) and the like), hormones, EVs and so forth.

In an example, the intercellular communication messenger, such as a cytokine, released by a cell of a first recipient cell population may induce a direct communication comprising modulation of a second recipient cell population in response to presence or absence of a modulator or intercellular communication between two or more cells. Alternatively, cytokine released by the cell of a third recipient cell population may induce an indirect communication comprising modulation of the second recipient cell population in response to: a modulator, a direct communication between the cytokine releasing cells of the third recipient cell population with that of the cytokine releasing cells of the first recipient cell population or a combination thereof.

The modulator is a compound interacting, either directly or indirectly, with one or more cells in order to alter the intercellular communication or cell-cell interaction. Optionally, the modulator is at least one of a biological entity, a chemical entity, a physical entity, environmental stimuli, and the like. More optionally, the modulators include, but are not limited to, growth factors, cytokines, drugs, ions, neurotransmitters, hormones, adhesion molecule, antibodies, natural compounds, proteins, carbohydrates, interferons (IFN), antigen presenting cells (APC), T cell modulators, B cell modulators, Superantigens (SAg), toll-like receptor (TLR) modulators, combinations of modulators (such as CD3/CD28 agonists), and so forth. Furthermore, the activation or deactivation of the intercellular communication or cell-cell interaction in the presence of the modulator is measured relatively as a percentage or a fold increase or decrease in activation of an activatable entity within the cells of various recipient cell populations. In an example, the modulator, such as an antigen presenting cell (APC) like a dendritic cell or a macrophage, does not interact (or does not substantially interact) with the recipient cell population, such as T-cells or B-cells. Nonetheless, other types of modulators are also possible, such as T cell activator (TCR) for example, which interact with one type of recipient cell population (such as T cells) but do not interact with any other type of recipient cell population (such as B cells) present in a culture of cells. The term "activatable entity" used herein relates to an entity that occurs in at least two distinguishable states, such as in either ON or OFF state. Optionally, the activatable entity forms a part of the recipient cell, for example, a site associated with a cellular protein, lipid, carbohydrate, or other constituent of the recipient cell. In an example, an activatable entity, such as a phosphorylation site on a protein may be in its ON (or active) state only when phosphorylated. In an embodiment, the activatable entity may be activated in response to chemical additions and physical and biological modifications such as acetylation, acylation, dephosphorylation, glycosylation, hydrolysis, isomerization, methylation, nitration, phosphorylation, and so forth. In another example, the activatable entity is a protein that can be activated by internal or external stimuli, such as a change in its conformation, binding affinity, translocation, cleavage, and so on.

Throughout the present disclosure, the term "recipient cell" used herein relates to at least one cell receiving information (biomaterial, biocomponent) from a donor cell, wherein the biomaterial can be EVs and their cargos, soluble ligands internalized within their plasma membrane receptor or viral entities. The donor cell type can be a healthy, normal cell or a transformed cell as compared to the recipient cell. Typically, the recipient cell is a somatic cell, preferably derived from a human. The recipient cells include, but are not limited to, blood cells, mesenchymal stromal cells, bone cells, muscle cells, epithelial cells, endothelial cells, immune cells, dendritic cells, somatic cells, germ cells, cells derived from any organs (such as pancreas, lungs, stomach, heart, spleen, kidney, thymus, cornea, bladder, esophagus, skin and so forth), and so on. In certain diseases such as retinal degeneration, diabetes, neuronal diseases and so on, donor cells are affected cells showing non-normal biological processes. Typically, the donor cell is a transformed cell such as a cancer cell or infected cell. Donor cell can also be healthy cell communicating with transformed cell.

In an embodiment, the recipient cell receives (biomaterial, biocomponent) from a donor cell, wherein the biomaterial can be EVs and their cargoes, soluble ligands internalized within their plasma membrane receptor or virus, but not limited to it. In another embodiment, the recipient cell and the donor cell are derived from same species or different species from the same genus. In yet another embodiment, the recipient cell receives whole or part of constituents from at least one of: a chemical compound, a chemotherapeutic compound, a drug and the like, by contacting or mixing together the recipient cell with the at least one of: a chemical compound, a chemotherapeutic compound, a drug and the like.

The term "recipient cell population" used herein relates to a group of cells with same cell-type or same characteristic. Specifically, recipient cell population comprises cells with the same or substantially the same set of surface markers (such as transcription factors, proteins, fluorescent markers) specific to a cell type, wherein such set of surface markers are known in the art. In an example, a recipient cell population is a stem cell population, and various subpopulations of the stem cell, such as embryonic stem cells, cardiac stem cells, hematopoietic stem cells and so on are characterized by different sets of cell surface markers. For example, the embryonic stem cells have Oct-4 (or Oct-3 or Oct-3/4) markers and the hematopoietic stem cells have CD34, CD133, ABCG2 and Sca-1 markers. Numerous recipient cell populations can be simultaneously the targets of EVs, soluble ligands or virus.

The term "culture of cells" or "culture of recipient cell population" relates to cultures containing a plurality of recipient cell populations in communication. Optionally, the culture of cells is derived from at least one sample obtained from the multicellular organism. In an embodiment, the multicellular organism is a normal individual, specifically a mammal, more specifically a human. In another embodiment, the multicellular organism is an individual (namely, a patient) with a condition (such as cancer, AIDS, tuberculosis and so forth). The sample may be obtained once or multiple times from the multicellular organism, namely normal sample from the normal individual and pathogenic sample from the individual with a condition. Furthermore, the sample may be a single or multiple sample(s) obtained from different location of the body of the multicellular organism. The multiple samples include, but are not limited to fluid samples (such as blood sample, bone marrow sample, lymph node sample, urine sample, serum sample, DNA sample, saliva sample, stool sample, semen sample, tear sample, sputum sample, menstrual blood sample, amniotic fluid and so on), effusions (such as from joints, peritoneal cavity, heart, and so on), solid tissue samples (such as biopsies, tissue scrapings, surgical specimens, stem cells, and so on), pathogenic cells (such as circulating tumor cells (CTC)) and so forth. In an embodiment, cells comprising different recipient cell populations are cultured in vitro in a growth media (such as a human-derived serum, a fetal bovine serum, a bovine serum, a goat serum, a horse serum, and so on). Subsequently, the cultured cells are exposed to one or more modulators.

Typically, the intercellular communication is mediated by receptor-ligand interaction, wherein the ligand is a signaling molecule and receptor is a receiving molecule attached to the cell membrane that is specific for one (or a few)

ligand(s). The receptor and ligand bind together by introducing functional and structural changes in the receptor that allows transmission of a signal through the recipient cell. Typical receptors include intracellular receptors occurring inside of the cell (such as in cytoplasm or nucleus) and cell surface receptors at the plasma membrane. The receptor-ligand interactions facilitate all biological processes such as signaling pathways occurring in unicellular or multicellular organisms.

Additionally, alternatively, intercellular communication is mediated by EVs. Throughout the present disclosure, the term "extracellular membrane vesicles (EVs)" used herein relates to small vesicles released from almost all types of multicellular organisms. Specifically, EVs serve as effective means for intercellular communication. More specifically, EVs transfer specific bioactive molecules, comprising functional mRNAs and microRNAs (miRNAs) across cells. Additionally, EVs protect biomolecules from degradation while allowing exchange of proteins, lipids, nucleic acids and so on between the donor cell and the recipient cell. In an example, EVs secreted by immune cells of central nervous system mediate intercellular communication between neurons, glia (or astrocytes) and microglia over long range distances. In another example, EVs associated with immune system allow exchange of antigen or major histocompatibility complex (MHC)-peptide complexes between antigen-bearing cells and antigen-presenting cells. For example, EVs secreted from B lymphocytes present MHC II-antigen complexes to T lymphocytes.

Furthermore, EVs are known to transport cytosolic material targeted for disposal out of the cells into the extracellular space or milieu. Typically, the cytosolic material includes, but is not limited to, (including proteins, lipids and RNAs). EVs are responsible for removing biomaterials that affect the cell at different sites and introducing the required supplements. For example, EVs are responsible for eliminating transferrin receptor and/or integrins from reticulocytes, which are not required by differentiated red blood cells.

It would be appreciated that the intercellular communication and the cytosolic waste management is mediated by two types of EVs, exosomes and ectosomes/microvesicles (MVs). The exosomes are small membrane-bound vesicles ranging from 30 to 100 nm in size and released from the cell surface by exocytosis. Specifically, exosomes are generated from membrane invaginations in the endosomal system to form intraluminal vesicles (ILVs) inside the late endosomes and/or multivesicular bodies (MVBs), which fuse with the plasma membrane to release mature ILVs, called exosomes, into the extracellular spaces or milieu. For instance, exosomes are released in body fluids such as urine, saliva, tears, blood, seminal and cerebrospinal fluids. Every internal and external body fluids can contain exosomes or other EVs. Every internal and external body fluids can content exosomes or other EVs. Typically, the exosomes mimic the molecular constituents of their cell of origin (donor cells), and contain soluble and membrane proteins, lipids, and nucleic acids such as messenger RNAs (mRNA), miRNAs, long non-coding RNAs and the like. The physiological conditions of donor cells might pre-determine the content of exosomes and their numbers. The exosomal-associated mRNAs are subsequently translated into functional proteins, and miRNAs effect gene silencing in the recipient cells. Exosomes are also known to elicit biological effects due to the presence of surface receptors or ligands for selective interaction with specific targets ligands or receptors of target cells (host cell or recipient cell) in multicellular organism. Thus, exosomes mediate transfer of molecules between two or more cells via extracellular trafficking of membrane vesicle. In an embodiment, exosomes may also play a functional role in mediating transport of tumor-associated molecules or tumor constituents and pathogens across multicellular organism, thereby affecting the immune system or other physiological systems. Therefore, it is a potential area of research to explain various biological processes associated with intracellular signaling and tumor growth and pathogenesis. Generally, the content and the number of EVs, especially the exosomes are influenced by physiological conditions and the cues coming from extracellular environment, however, the membrane-embedded exosomes are highly stable in extracellular space due to the presence of relatively higher concentrations of cholesterol, sphingomyelin and membrane nano-microdomains in its lipid bilayer. Therefore, high stability of exosomes in bodily fluids makes them highly efficient as potential disease marker.

Another class of extracellular EVs includes the MVs. Various types of MVs were described. The MVs originate from the outward budding or fission of the plasma membrane of the cell. They can bud from plasma membrane protrusions, such as microvilli, cilia and filopodia, or the non-protruding regions of plasma membrane. Other MVs are apoptotic bodies, which are released upon cell fragmentation during apoptotic cell death, as well as large oncosomes when shed from non-apoptotic membrane blebs of tumor cells. The MVs range from 50 nm to 10 μm in size dependent of their origin. The MVs are highly heterogenous in size, shape and content. MVs contain membrane proteins and phospholipids shed from various cell types. Like the exosomes, the MVs also play a functional role in intercellular communication and transport of biomaterial, such as proteins, lipids and nucleic acids including mRNA and miRNA from one cell to another. In an embodiment, the MVs are known to play a primary role in transfer of pathogens and tumor antigens into the recipient cells. In another embodiment, MVs are released from the endothelial cells, epithelial cells, smooth muscle cells, white blood cells, platelets and red blood cells leading to inflammatory and pathological diseases including, but not limited to, hypertension, cardiac ailments, neurodegenerative disorders, diabetes and rheumatoid arthritis. Additionally, changing levels of MVs in various diseases, for example such as cancer, rheumatoid arthritis, neurological disorder, makes it a potential biomarker in a variety of diagnostic analysis. In an example, Alzheimer's disease can be diagnosed in patients at a relatively early stage by measuring the increased levels of phosphorylated Tau proteins, or epilepsy is associated with increased levels of CD133 in MVs of the patients with epilepsy.

Furthermore, the EVs deliver the biocomponents through the nuclear membrane into nucleoplasm of the recipient cells. The nuclear membrane (or nuclear envelope) is a double lipid bilayer, comprising an inner nuclear membrane (INM) and an outer nuclear membrane (ONM) separated by a perinuclear space. Specifically, the nuclear membrane physically separates the nucleoplasm and cytoplasm of the cell. The nuclear membrane encloses various components in the nucleoplasm including genetic materials and the like, contributing to nuclear structural integrity of the cell. It will be appreciated that the lipid bilayer composition of the nuclear membrane also comprises other bioactive components, such as proteins (e.g., those found in nuclear pores, and forms a network of invaginations, such as nucleoplasmic reticulum (NR) and so forth.

Specifically, the EVs-derived biocomponents are delivered into the nucleoplasm of the recipient cells through small holes and/or channels called nuclear pores in the nuclear membrane. More specifically, the nuclear transfer of EVs-derived biocomponents occurs through the nuclear pores. Other unidentified mechanisms of transfer are not excluded in the state of art. Furthermore, membrane protein and/or combinations thereof (namely, protein complexes) play a vital role in nuclear transfer of EVs-derived biocomponents. Such protein complexes include, but are not limited to, a tripartite VAP-A, ORP3 and Rab7 (VOR) protein complex. Specifically, the tripartite VOR protein complex comprises an ER-localized vesicle-associated membrane protein-associated protein A (VAP-A), a cytoplasmic oxysterol-binding related protein 3 (ORP3) and a late endosome (LE)-associated small GTPase Rab7 in the NEI. More specifically, the tripartite VOR protein complex specifically localizes late endosomes (indicated by "LE" hereafter) into the NR and are essential for the nuclear transfer of EV-derived biocomponents. Nonetheless, the components of the tripartite VOR protein complex is not only found in the NEI, but also widely distributed across the cytoplasm. Specifically, the VAP-A and Rab7 pair is distributed across the cytoplasm. Furthermore, interaction of the VAP-A with the ORP3 mediates the localization of the Rab7 into the ONM, where they allow the transfer of the biomaterials to the nucleoplasm.

Notably, VAP-A is also associated with the presence of the ORP3 in the NEI. Specifically, the VAP-A interacts with the peripheral LE multi-domain oxysterol-binding protein (OSBP)-related protein 1L (ORP1L) that binds to small GTPase Rab7. It will be appreciated that silencing the binding of VAP-A to ORP3 prevents the association of Rab7+ LE with the nuclear envelope invaginations (NEI), and hence, the transfer of endocytosed EV-derived components to the nucleoplasm of recipient cells. Moreover, VAP-A has a homologue, VAP-B, however, VAP-B is not required for the presence of LE in the NEI. Furthermore, silencing of VAP-B does not affect the expression of VAP-A.

Therefore, the inhibition of EV-mediated intercellular communication can have therapeutic potential for cancer and other diseases such as viral infection associated with a dysregulation of the EVs based on change in their values under pathological conditions. It will be appreciated that like any other cells, the cancerous cells also secrete EVs. Specifically, cancer cells (or the malignant tumor cells) secrete more EVs as compared to normal cells or benign tumor cells (counterpart of the malignant tumor cells). Furthermore, EVs secreted by cancerous cells are critical mediators of the intercellular communication between the cancerous cells and the recipient cells of the multicellular organisms. Typically, EVs facilitate various pathophysiological processes, such as coagulation, vascular leakage, pre-metastatic niche formation and metastasis at various sites in different tumor microenvironments. Therefore, by monitoring the change in levels of EVs, EVs serve as potential biomarkers and novel therapeutic targets against cancer progression and associated metastatic development. In an embodiment, EVs also serve as a potential vehicle for the delivery of therapeutic agents or drugs against cancer.

Furthermore, intracellular communication is also responsible for various pathological conditions, such as a viral infection and so forth. The viral infection involves the transport of endocytosed biomaterials to the nucleus of recipient cells. Specifically, like the cancerous cells, virus-infected cells also secrete EVs, thus large numbers of EVs are secreted during viral infection. Specifically, viral particles, proteins and RNA, are transferred from a viral cell into nucleus of the recipient cell via the endosomal system. Nonetheless, the viral cells also secrete virions along with the secretion of EVs. Generally, the viruses are non-living organisms outside a host cell, however, they lead a normal reproductive live inside the host. In light of the aforesaid, the viral cells deploy both the EVs and the virions for transferring the viral biocomponents into the recipient cells. Majorly, the viral cells exploit the EVs to transport viral proteins (namely, Nef and Gag), fragments of viral genome (RNA) and viral miRNA to the genetic machinery of the recipient cell for sustainable growth of the viral biocomponents inside the multicellular organisms, thereby affecting the viral infection. In an embodiment, the EVs suppress viral infection by attaching to viral particles, thereby reducing the release of virions that infect immune cells of the recipient cells, such as CD4+ T cells.

In an embodiment, EVs serve as potential biomarkers and novel therapeutic targets against cancer and viral infection. In another embodiment, EVs also serve as a potential vehicle for the delivery of therapeutic agents or drugs against various diseases, such as cancer, and pathological conditions, such as viral infection, preferably AIDS.

The present disclosure provides a compound selected from triazole analogues or pharmaceutically acceptable salt, hydrate, solvate or prodrug thereof for use in inhibiting a tripartite VAP-A, ORP3 and Rab7 (VOR) protein complex in multicellular organisms by interfering with at least one mechanism of intercellular communication, wherein the intercellular communication is mediated by receptor-ligand interaction and/or EVs; and viral infection involving the transport of endocytosed biomaterials to the nucleus of recipient cells is provided.

Specifically, the some triazole analogues compounds, like itraconazole (hereafter ICZ) and ketoconazole inhibit the growth of fungi. More specifically, it prevents the fungi from producing the membrane that surrounds the fungal cells. However, the triazole analogues have a broader spectrum of activity than just as an antifungal agent.

Differently from other triazole compounds, such as itraconazole ICZ and ketoconazole, the triazole analogues do not inhibit the growth of fungi because they completely lack the chemical groups responsible for the anti-fungal activity. Instead, they inhibit the tripartite VOR protein complex by either interfering with the mechanism of intercellular communication mediated by the receptor-ligand interaction and/or the EVs, and/or transport of endocytosed biomaterials to the nucleus of recipient cells. More specifically, the triazole analogues prevent the binding of Rab7 to ORP3, thereby blocking penetration of Rab7+ late endosomes containing EVs or HIV-1 virus into the nuclear envelope invaginations NEIs and thus the transfer of their bio-components into the nucleus. Furthermore, the triazole analogues or any modifications of their molecules, such as their salts, may be more specific and potent inhibitors as anti-cancer and anti-viral drugs.

In accordance with embodiments of the present disclosure, the triazole analogues are analogues in which have the following structures:

Formula I

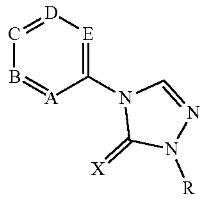

wherein,

A, B, C, D, E are each independently selected from $CR^1$ or N;

R is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, haloalkyl, haloalkenyl, haloalkynylalkyl, haloalkoxy heteroalkyl, heterocycloalkyl, heteroaryl, heteroarylalkyl, heterocycloalkylalkyl, alkylsulfonyl and any optical substitutes thereof; and X is selected from O, S and $CH_2$.

In an embodiment, the $R^1$ is selected from the group consisting of hydrogen, alkyl, arylalkyl, alkoxyalkyl, arylalkoxy, alkynylalkyl, alkylalkynylalkyl, alkenylalkyl, alkylalkenylalkyl, amino, amido, cycloalkyl, cyanoalkyl, cycloalkylalkyl, halogen, haloalkyl, haloalkenyl, haloalkynylalkyl, haloalkoxy, nitro and any optical substitutes thereof.

In another embodiment, the triazole analogues has the following structure of Formula II or an optically pure stereoisomer or pharmaceutically acceptable salt, hydrate, solvate or prodrug thereof:

Formula II

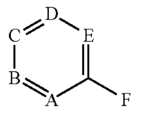

wherein,

A, B, C, D, E are each independently selected from $CR^1$ or N; and $R^1$ is selected from the group consisting of hydrogen, alkyl, arylalkyl, alkoxyalkyl, arylalkoxy, alkynylalkyl, alkylalkynylalkyl, alkenylalkyl, alkylalkenylalkyl, amino, amido, cycloalkyl, cyanoalkyl, cycloalkylalkyl, halogen, haloalkyl, haloalkenyl, haloalkynylalkyl, haloalkoxy, nitro and any optical substitutes thereof.

In an embodiment, the F is selected from the group consisting of:

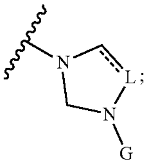
;
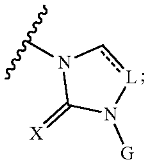
;
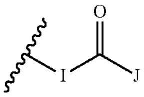
;

-continued

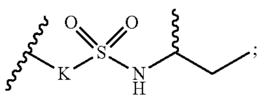
;
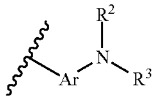

wherein, $\overline{---}$ is a single or a double bond.

Further, the L is selected from $CH_2$, CH and NH; the G is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, haloalkyl, haloalkenyl, haloalkynylalkyl, haloalkoxy heteroalkyl, heterocycloalkyl, heteroaryl, heteroarylalkyl, heterocycloalkylalkyl, alkylsulfonyl and any optical substitutes thereof; the X is selected from O, S and $CH_2$; the I is selected from $(CH_2)_mCH_3$ and $NR^4$; the J is $(CH_2)_nCH_3$ and $NR^5R^6$; the $R^4$ is selected from H, unsubstituted C1-6 alkyl and substituted C1-6 alkyl; the $R^5$ is selected from H, unsubstituted C1-6 alkyl, substituted C1-6 alkyl; the $R^4$ and $R^5$ are joined to form an unsubstituted or substituted 5- or 6-membered ring with the —N-(=J)-N— moiety, wherein the $R^4$ and $R^5$ form a unsubstituted or substituted $C_{2-3}$ carbohydryl group or a unsubstituted or substituted $C_{1-2}$ carbohydryl group linked via a nitrogen to a nitrogen of the —N-(=J)-N— moiety; the $R^6$ is selected from H, substituted or unsubstituted $C_{1-6}$ alkyl, $C_{1-6}$ alkoxy, $C_{2-6}$ alkanoyl, $C_{1-6}$ alkoxcarbonyl, and $C_{1-6}$ haloalkyl; the K is selected from $(CH_2)_p$ and NH, specifically, the n, m, p are independent integers between 0 to 4, and Ar is selected from unsubstituted aryl and substituted aryl; the $R^3$ is selected from —C(=O)—$R^7$, —C(=O)—O—$R^7$, and —$S(=O)_n$—$R^7$, wherein the n ranges between 0 to 3, and wherein the $R^7$ is selected from the group consisting of hydrogen, alkyl, arylalkyl, alkoxyalkyl, arylalkoxy, alkynylalkyl, alkylalkynylalkyl, alkenylalkyl, alkylalkenylalkyl, cycloalkyl, cyanoalkyl, cycloalkylalkyl, heteroalkyl, heterocycloalkyl, heteroaryl, heteroarylalkyl, heterocycloalkylalkyl, alkylsulfonyl, and any optical substitutes thereof; the $R^2$ and $R^3$ along with the nitrogen atom form a nitro ($NO_2$) group; the $R^2$ and $R^3$ are joined to from an unsubstituted or substituted 5- or 6-membered ring with the proviso excluding a —N—(=Z)—N— moiety, wherein the Z is selected from O and S.

In accordance with embodiments of the present disclosure, the triazole analogues include all possible enantiomers and diastereoisomers of the triazole analogues and or pharmaceutically acceptable salt, hydrate, solvate or prodrug thereof.

In accordance with embodiments of the present disclosure, the triazole analogues or pharmaceutically acceptable salt, hydrate, solvate or prodrug thereof for use in inhibiting a tripartite VAP-A, ORP3 and Rab7 (VOR) protein complex in multicellular organisms are selected form the compounds as disclosed in below mentioned Table-1.

TABLE-1

| Structure | Compound Number |
|---|---|
| 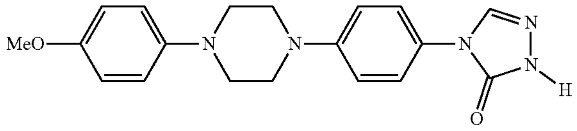 [SMILES: COc1ccc(N2CCN(c3ccc(-n4cn[nH]c4=O)cc3)CC2)cc1] | PRR844 |

TABLE-1-continued
| Structure | Compound Number |
|---|---|
| 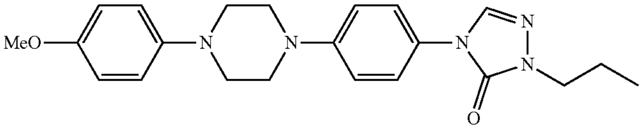 [SMILES: CCCn1ncn(-c2ccc(N3CCN(c4ccc(OC)cc4)CC3)cc2)c1=O] | PRR845 |
| 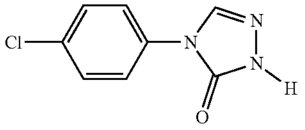 [SMILES: O=c1[nH]ncn1-c1ccc(Cl)cc1] | PRR846 |
| 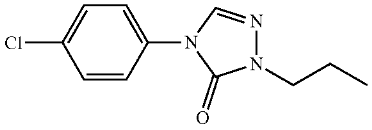 [SMILES: CCCn1ncn(-c2ccc(Cl)cc2)c1=O] | PRR850 |
| 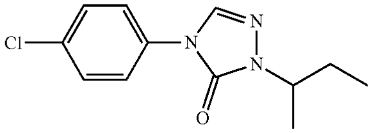 [SMILES: CCC(C)n1ncn(-c2ccc(Cl)cc2)c1=O] | PRR851 |
| 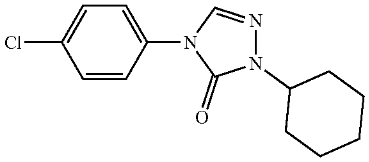 [SMILES: O=c1n(-c2ccc(Cl)cc2)cnn1C1CCCCC1] | PRR861 |
| 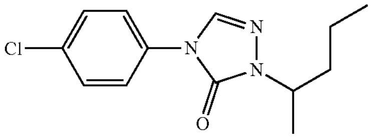 [SMILES: CCCC(C)n1ncn(-c2ccc(Cl)cc2)c1=O] | PRR862 |
| 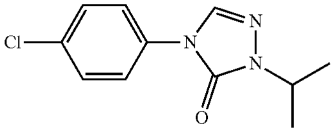 [SMILES: CC(C)n1ncn(-c2ccc(Cl)cc2)c1=O] | PRR863 |
| 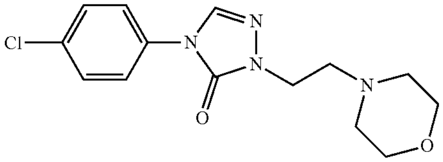 [SMILES: O=c1n(-c2ccc(Cl)cc2)cnn1CCN1CCOCC1] | PRR867 |
| 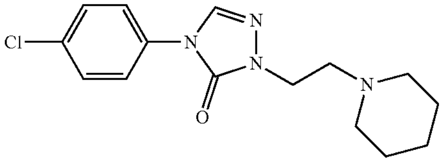 [SMILES: O=c1n(-c2ccc(Cl)cc2)cnn1CCN1CCCCC1] | PRR868 |
| 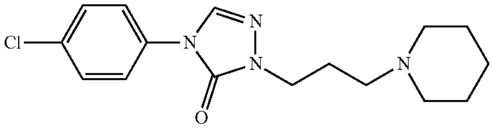 [SMILES: O=c1n(-c2ccc(Cl)cc2)cnn1CCCN1CCCCC1] | PRR869 |

TABLE-1-continued
| Structure | Compound Number |
|---|---|
| 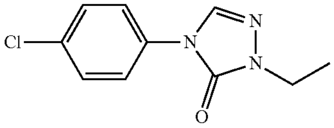 | PRR870 |
| 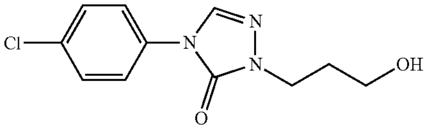 [SMILES: O=c1n(-c2ccc(Cl)cc2)cnn1CCCO] | PRR871 |
| 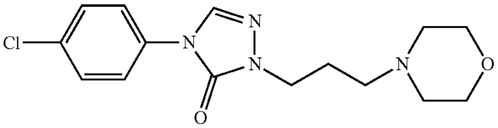 [SMILES: O=c1n(-c2ccc(Cl)cc2)cnn1CCCN1CCOCC1] | PRR873 |
| 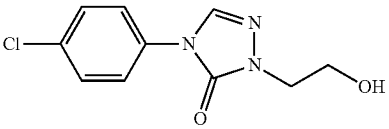 [SMILES: O=c1n(-c2ccc(Cl)cc2)cnn1CCO] | PRR874 |
| 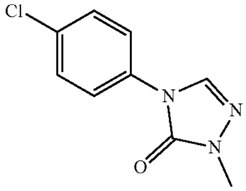 | PRR888 |
| 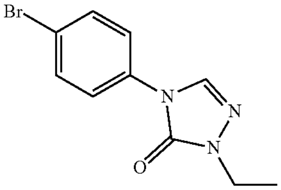 | PRR901 |
| 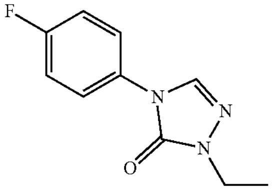 | PRR902 |
| 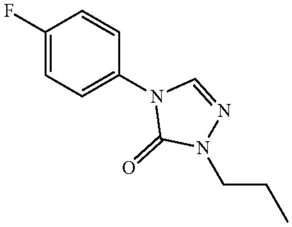 [SMILES: CCCn1ncn(-c2ccc(F)cc2)c1=O] | PRR903 |

TABLE-1-continued
| Structure | Compound Number |
|---|---|
| 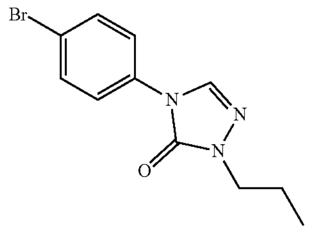 [SMILES: CCCn1ncn(-c2ccc(Br)cc2)c1=O] | PRR904 |
| 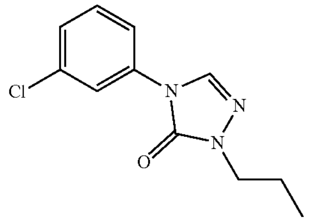 [SMILES: CCCn1ncn(-c2cccc(Cl)c2)c1=O] | PRR896 |
| 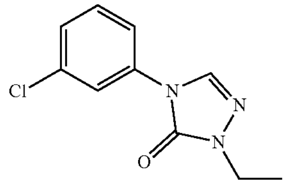 | PRR895 |
| 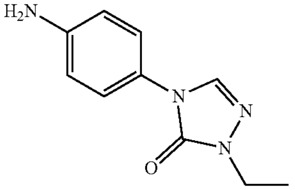 | PRR890 |
| 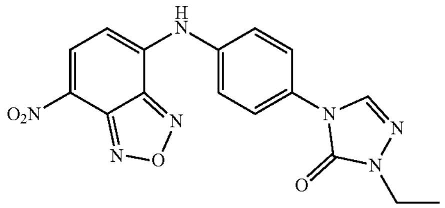 [SMILES: CCn1ncn(-c2ccc(Nc3ccc([N+](=O)[O-])c4nonc34)cc2)c1=O] | PRR898 |
| 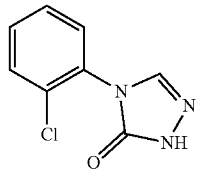 [SMILES: O=c1[nH]ncn1-c1ccccc1Cl] | PRR893 |
| 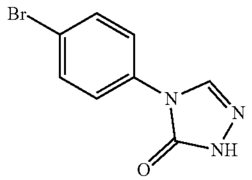 [SMILES: O=c1[nH]ncn1-c1ccc(Br)cc1] | PRR900 |

TABLE-1-continued

| Structure | Compound Number |
| --- | --- |
| 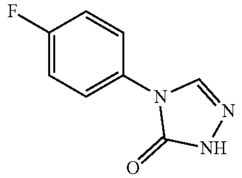 [SMILES: O=c1[nH]ncn1-c1ccc(F)cc1] | PRR899 |

Optionally, the compound selected from triazole analogues or pharmaceutically acceptable salt, hydrate, solvate or prodrug thereof is for use in the treatment or prevention of a disease or condition in which the VOR complex is implicated. Specifically, the compound selected from triazole analogues or pharmaceutically acceptable salt, hydrate, solvate or prodrug thereof is used to inhibit the tripartite VOR protein complex associated with disease such as cancer or condition such as viral infection. As mentioned previously, the compound selected from triazole analogues or pharmaceutically acceptable salt, hydrate, solvate or prodrug thereof is a potential anti-cancer and anti-viral agent, therefore it is used in the treatment or prevention of a disease or condition in which the VOR complex is implicated.

Optionally, the compound is used in treatment and prevention of cancer and cancer metastasis. Specifically, cancer is caused by cancerous cells (or carcinoma or carcinogenic cells or tumors), especially the malignant cancer/tumor cells. The counterpart of the malignant cancer/tumor cells are benign tumor cells that do not cause cancer. More specifically, the cancerous cells possess potential to invade the neighboring cells and spread over different parts of the body of a multicellular organism. Specifically, diseases like cancer are characterized by an unregulated cell growth. The growth of cancer involves various stages including, but not limited to, pre-metastatic niche formation and metastasis at various sites in different tumor microenvironments. Cancer metastasis refers to the distant growth of cancer, i.e. the potential of cancerous cells to spread from one part to another and in the process arranging for resources (from the host cell) supporting its growth. Therefore, the present method comprises the use of potential anti-cancer agents against the metastatic process, i.e. the dissemination of cancer cells.

According to the Human Protein Atlas, ORP3, the direct target of triazole analogue in the VOR complex, is highly expressed in kidney, bladder and endometrium, the organs of origin of kidney, bladder and endometrial carcinomas. Therefore, the cancer optionally includes at least one of a kidney carcinoma, a bladder carcinoma, and an endometrial carcinoma. Given that almost all tumors express ORP3, the triazole analogues or salt thereof thus have potential activity in all types of cancer.

Optionally, the triazole analogues or pharmaceutically acceptable salt, hydrate, solvate or prodrug thereof are used in treatment or prevention of an infectious disease. Specifically, such infectious disease is due to a pathological condition. More specifically, the pathological condition or the infectious disease may be caused due to various pathogens including, but not limited to, a bacterium, a virus, a fungus, a protozoan, and so forth. The treatment or prevention of the infectious disease requires targeting the pathogen, the bacteria, the virus, the fungus and/or the protozoan.

Optionally, the disease is caused by a virus. A virus is a small infectious agent. Generally, viruses are non-living organisms outside a host cell, however, they lead a normal reproductive live inside the host. Specifically, the virus replicates only inside the living cells of other organisms, such as animals, plants, humans, bacteria, and so forth. The viral infection involves the transport of endocytosed biomaterials to the nucleus of recipient cells. More optionally, the virus is HIV-1. The HIV-1 is a virus that attacks immune system of the host organism (or recipient cell), specifically CD4 cells. HIV-1 causes a viral infection, namely AIDS, which severely damages the immune response of the host organism. Specifically, like the cancerous cells, virus-infected cells also secrete EVs, thus large numbers of EVs are secreted during viral infection. More specifically, viral particles, proteins and RNA, are transferred from a virus-infected cell into nucleus of the recipient cell via the EVs, especially the MVs. Moreover, the HIV pre-integration complex needs to be translocated to the nucleus and this process may require the VOR complex. Nonetheless, the viral cells also secrete virions, along with the EVs, for transferring the viral biocomponents into the recipient cells. Nevertheless, HIV virus can counteract its inhibition by EVs by incorporating HIV-Nef into the EVs, decreasing the host's antiviral response. Therefore, there exists means for inhibiting the intercellular communication that leads to progression of cancer and other pathological diseases such as AIDS or other viral infections.

Optionally, the virus is any enveloped virus that is transported intracellularly by the endosomal system. Optionally, the virus is any virus that requires some biomolecules to be transported into the nuclear compartment for its own replication.

In an embodiment, the compound selected from triazole analogues or pharmaceutically acceptable salt, hydrate, solvate or prodrug thereof is used in treatment of at least one of: a neurodegenerative disease, a ventricular hypertrophy, a type I diabetes, a type II disease, a retinal degeneration including macular degeneration, a lung disease or any other disease whose pathogenesis involves EVs. The EV-mediated intercellular communication is also implicated in various conditions including, but not limited to, neurodegenerative disease, a ventricular hypertrophy, a type I diabetes, a type II disease, a retinal degeneration and a lung disease. Typically, the neurodegenerative disease includes Alzheimer's disease, Parkinson's disease and so on. Specifically, the neurodegenerative diseases target the neurons or nerve cells in the neural system. Similarly, the ventricular hypertrophy, the type I and/or type II diabetes, the macular degeneration and the lung disease are associated with specific cell types, such as a cardiac cell, a pancreatic cell, a renal cell, a cone cell and an alveolar macrophage cell. Furthermore, the EVs contain various associated proteins specific for a viral disease. For example, the EVs contain neurodegenerative disease-associated proteins such as a prion protein, a beta amyloid, an alpha-synuclein, a tau protein and the like.

Optionally, the compound selected from triazole analogues or pharmaceutically acceptable salt, hydrate, solvate or prodrug thereof may be consumed orally or administered intravenously. However, other suitable route of administration can be employed, for example transdermal, topical, parenteral, ocular, vaginal, rectal, buccal, lingual, intranasal and inhalation. For the purpose of the present invention, the triazole analogues or pharmaceutically acceptable salt, hydrate, solvate or prodrug thereof may be preferably administered by the oral route. Specifically, the oral administration of the triazole analogues or pharmaceutically acceptable salt, hydrate, solvate or prodrug thereof includes but is not limited to capsules, tablets, powders, pellets, syrups, concoctions, and so on.

Furthermore, the dose of the triazole analogues or pharmaceutically acceptable salt, hydrate, solvate or prodrug thereof depends on various parameters, such as the nature and degree of the condition, body weight, age, general health, diet followed, gender, frequency of administration, duration of treatment, any other drug prescribed or consumed, and so forth. The frequency of administration may range from once, twice or more often each day. Additionally, the duration of treatment relates to the total amount of time for which the treatment is provided. Optionally, the triazole analogues or pharmaceutically acceptable salt, hydrate, solvate or prodrug thereof are administered orally at a total daily dose of 200-800 mg twice a day. More optionally, the oral doses of triazole analogues or pharmaceutically acceptable salt, hydrate, solvate or prodrug thereof are provided for a minimum of 14 days and a maximum of six months. It will be appreciated that a classical formulation of triazole analogues or pharmaceutically acceptable salt, hydrate, solvate or prodrug thereof or a super-bioavailability formulation will be administered. In general, the dose of the super-bioavailability will be 50% of the classical formulation.

DESCRIPTION OF DRAWINGS

Referring to FIGS. 1A, 1B and 1C, illustrate data showing the localization and tripartite structure of a VOR complex. Notably, the VOR complex is localized in the NEI. Typically, EVs are transported to late endosomes after their endocytosis, wherein the EVs facilitate intercellular communication in diverse cellular processes. Furthermore, the lack of the NEI-associated late endosomes and the inhibition of transfer of EV-derived components into the nucleoplasm of host cells after importazole treatment depict the role of nuclear pores and importin β1 in the processes. Moreover, the potential interaction between the VOR complex and/or the NEI-associated late endosomes may significantly assist the processes. Notably, such processes allow the extraction of EV-derived membrane proteins from endosomal membrane and the subsequent transfer of EV-derived membrane proteins into the nucleoplasm through the nuclear pores of the host cells.

Referring to FIG. 1A, illustrates the major compartment involved in the present application, i.e. the nucleus with the type II NEI formed by the inner and outer nuclear membranes. VOR complex is associated with type II NEI.

Referring to FIG. 1B, illustrates a schematic diagram of $Rab7^+$ late endosomes in type II NEI. Typically, the presence of $Rab7^+$ late endosomes in NEI requires VAP-A and ORP3. Furthermore, the presence of ORP3 is aided by VAP-A. Moreover, the protein VAP-A is associated with the outer nuclear membrane of type II NEI as well as endoplasmic reticulum.

Referring to FIG. 1C, illustrates a schematic drawing of the VOR complex proteins. Notably, the VOR complex contains the proteins VAP-A, ORP3 and Rab7. Typically, the VOR complex allows the tether of late endosomes to outer nuclear membrane including type II NEI.

Referring to FIG. 2, illustrates the interactions between VAP-A, ORP3 and Rab7. The detergent lysates prepared from melanoma FEMX-I cells (left panels) or colon SW480 cells (right panels) are subjected to immunoisolation (IS) with anti-ORP3 antibody. Furthermore, the process of interaction is assisted by Protein G-coupled magnetic beads. Then, entire bound fractions are probed for ORP3, VAP-A/B, and Rab7 by immunoblotting. As shown, the molecular mass markers (kDa) are indicated for each of the interaction. Arrows indicate the protein of interest and the consequent representative blots are depicted. It will be appreciated that no VAP-B is co-immunoisolated with ORP3 in contrast to VAP-A. The specificity of immunoisolation was confirmed with anti-GFP antibody or the absence of primary antibody (right panels).

Referring to FIG. 3A, B, illustrates the structure of compounds 3 and 5 and the VOR complex inhibition. (A) The structures of ICZ, ketoconazole, compound 3 (4-(4-Chlorophenyl)-2,4-dihydro-3H-1,2,4-triazol-3-one) and compound 5 (2-(butan-2-yl)-4-(4-chlorophenyl)-2,4-dihydro-3H-1,2,4-triazol-3-one) drugs are displayed. The reactive groups in ICZ are indicated (dashed boxes). Compound 3 was produced from 4-chloroaniline treated with triethyl orthoformate p-toluenesulphonic acid, methyl carbazate and sodium methoxide in methanol (reaction i), while compound 5 was generated from the N-alkylation of compound 3 with 2-bromobutane in the presence of sodium carbonate and 18-crown-6, 2-bromobutane in DMSO (reaction ii). (B) Homology model of ORP3 ORD with the putative drug complex as computed by docking simulations for ICZ (top panel), compounds 3 and 5 (middle panels) within the binding cavity. A composite image compares the simulation of each compounds (bottom panel).

Referring to FIG. 4, illustrates the impact of the triazole compound 5, but not compound 3, on the VOR complex integrity. SW480 cells were incubated with DMSO solvent alone (control), 10 μM ICZ, triazole compound 5, compound 3 or ketoconazole for 5 hours, solubilized and subjected to immunoisolation (IS) using anti-ORP3 Ab followed by Protein G-coupled magnetic beads. The input (1/50, for Rab7 only) and entire bound fractions were probed by immunoblotting for ORP3, VAP-A and Rab7. The Rab7/VAP-A ratios were quantified (n=3). The mean±S.D. are shown. P values are indicated. Note that ICZ and compound 5 inhibit the co-immunoisolation of Rab7, while compound 3 and ketoconazole do not. N.s., not significant.

Referring to FIG. 5, illustrates the impact of the triazole compound 5, but not compound 3, on the VOR complex integrity. Detergent SW480 cell lysates were incubated with DMSO solvent alone (control), 10 μM ICZ, triazole compound 5, compound 3 or ketoconazole for 30 minutes on ice, and then subjected to immunoisolation (IS) using anti-ORP3 Ab followed by Protein G-coupled magnetic beads. The input (1/50, for Rab7 only) and entire bound fractions were probed by immunoblotting for ORP3, VAP-A and Rab7. The Rab7/VAP-A ratios were quantified (n=3). The mean±S.D. are shown. P values are indicated. Compound 5 inhibits the co-immunoisolation of Rab7, while compound 3 and ketoconazole do not. N.s., not significant.

Referring to FIG. 6, illustrates the effects of increasing concentration of triazole compound 5 on the VOR complex integrity. SW480 cells were incubated with DMSO solvent alone (control), 10 μM ICZ or different concentrations of compound 5 as indicated for 5 hours, solubilized and subjected to immunoisolation (IS) using anti-ORP3 Ab and Protein G-coupled magnetic beads. The input (1/50) and bound fractions were probed by immunoblotting for ORP3, VAP-A and Rab7 (top panel). Molecular mass markers are indicated, and arrows point to the proteins of interest. The ratio of protein immunoreactivities of the indicated pairs was quantified (bottom panel, n=3). The mean±S.D. are shown. P values are indicated. N.s., not significant.

Referring to FIG. 7, illustrates the competition between the 25-hydroxycholesterol and triazole compound 5 to bind the hydrophobic pocket of the conserved C-terminal OSBP-related domain (ORD) of ORP3. In a competitive assay, detergent SW480 cell lysates were pre-incubated with 25-hydroxycholesterol (25-HC) at the indicated concentration for 30 minutes prior to the incubation with 10 μM ICZ or triazole compound 5 for 30 minutes on ice. As internal controls, cell lysates were treated for 1 hour with DMSO (control), 10 μM ICZ, 10 μM compound 5 or 100 μM 25-HC. Samples were solubilized and subjected to immunoisolation (IS) using anti-ORP3 Ab followed by Protein G-coupled magnetic beads. The entire bound fractions were probed by immunoblotting for ORP3, VAP-A and Rab7 (top panel). The molecular mass markers are indicated, and arrows point to the proteins of interest. The Rab7/VAP-A ratios were quantified (bottom panel). The mean±S.D. are shown. P values are indicated.

Referring to FIG. 8, illustrates that the triazole compound 5 inhibited the entry of $Rab7^+$ late endosomes in NEI. SW480 cells were incubated with DMSO (control), 10 μM ICZ, triazole compound 5, triazole compound 3 or ketoconazole (KCZ) for 5 hours prior to double immunolabelling for Rab7 and nuclear membrane protein SUN2 and the staining with cholesterol-binding compound filipin. Cells were analyzed by confocal laser scanning microscopy (left panel). Arrows indicate $SUN2^+$ NEI and arrowheads point to Rab7 and filipin-labelled cholesterol therein. Note the absence of Rab7 and cholesterol in $SUN2^+$ NEI after ICZ or compound 5 treatment. Bar graph shows the percentage of $SUN2^+$ NEI containing $Rab7^+$ late endosomes (LE) (right panel). The mean±S.D. are shown. P values are indicated. N.s., not significant. Scale bars, 5 μm.

Referring to FIG. 9, illustrates that the triazole compound 5 inhibited EV-induced pro-metastatic morphological transformation. SW480 cells were pre-treated with DMSO solvent alone (control), 10 μM ICZ, triazole compound 5 or compound 3 for 10 minutes prior to incubation without or with EVs ($1\times10^9$ particles/ml) derived from metastatic SW620 cells for 5 hours. Cell morphology was analyzed by confocal laser scanning microscopy upon CD9 immunolabelling (data not shown). Bar graphs show the percentage of cells harboring a rounded (left panel) or blebbed (right panel) morphology upon exposure to EVs. The mean±S.D. are shown. At least 50 cells were evaluated per condition and independent experiment (n=6). Note that ICZ and compound 5 inhibited the morphological transformation of SW480 cells induced by EVs derived from metastatic SW620 cells.

Referring to FIG. 10, illustrates that the triazole compound 5 inhibited the nuclear transfer of EV cargo. SW480 cells were pre-treated for 10 minutes with DMSO (control), 10 μM ICZ, triazole compound 5, triazole compound 3 or ketoconazole (KCZ) prior to 5-hour incubation with melanoma cell-derived CD9-green fluorescent protein $(GFP)^+$ EVs in the absence or presence of drugs. Recipient cells were then fixed and immunolabelled for the nuclear membrane protein SUN2. The amounts of EV-derived CD9-GFP in the nuclear compartments were analyzed by confocal laser scanning microscopy and quantified using Fiji software. Nuclear CD9-GFP was evaluated from 50 cells per condition and a representative experiment with mean±S.D. are shown. P values are indicated. N.s., not significant.

Referring to FIG. 11, illustrates that triazole analogues were not toxic for cells. Cancer SW480 cells (left panel) and primary mesenchymal stromal cells (right panel) were incubated with DMSO solvent alone (control), 10 μM ICZ, compound 5, compound 3 or ketoconazole (KCZ) for 24, 48 and 72 hours as indicated. At the end of each time point, MTS tetrazolium compound (3-(4,5-dimethylthiazol-2-yl)-5-(3-carboxymethoxyphenyl)-2-(4-sulfophenyl)-2H-tetrazolium) was added for 1 hour to evaluate the amounts of viable cells. The absorbance value was measured at 490 nm. The mean±S.D. are shown (n=6). **, $p<0.01$.

Referring to FIGS. 12A, 12B, 12C and 12D illustrate the effects of various triazole compounds on the VOR complex integrity. Detergent SW480 cell lysates were incubated with DMSO solvent alone (control), 2.5 μM (FIG. 12A), 5 μM (FIG. 12B), 7.5 μM (FIG. 12C) or 10 μM (FIG. 12D) ICZ and triazole compounds for 30 minutes on ice and then subjected to immunoisolation (IS) using anti-ORP3 Ab followed by Protein G-coupled magnetic beads. The entire bound fractions were probed by immunoblotting for ORP3, VAP-A and Rab7 (data not shown). The percent inhibition of Rab7 expression were quantified and compared to the control sample (dashed line). Many triazole compounds (2,4,5,7,8,10,12,13,15,17-23 and 26-27 can be seen to have inhibited Rab7 co-immunoisolation in varying degrees. The mean±S.D. are shown.

Referring to FIG. 13A, B, illustrates the impact of ICZ and compound 5 on the proximity of ORP3 and Rab7 in various subcellular zones. SW480 cells were treated with 10 μM ICZ or compound 5 or with DMSO (control) for 5 hours, fixed and the subcellular localization of ORP3 (green) and Rab7 (red) was analyzed by immunolabelling using 3D dSTORM. Whole cell images (A, left panels) and magnified areas (white boxes) of NEI, perinuclear and cytoplasm (A, right panels) are displayed. Corresponding Imaris-based, 3D-rendered images were reconstructed and a computer model was rendered to show the relative structure and distance between ORP3 and Rab7 with the heat map indicating their linear proximity (blue to green: 0 to 50 nm) (A). The distance between the total ORP3 molecules and Rab7 in each subcellular area was scored as inferior or superior to 10 nm and data plotted as percentage of total ORP3 in each cell (n=10 independent cells from 3 distinct experiments) (B). Scale bars, 5 μm (A, left panels) or 500 nm (A, right panels).

Referring to FIG. 14A-C, illustrates the 3D-rendered images from pericellular zone were reconstructed to illustrate the difference in volume of $Rab7^+$ structures of control compared with ICZ- and compound 5-treated cells (A, left). The volume of $Rab7^+$ structures greater than 20 $nm^3$ in the pericellular and perinuclear zones is depicted (n=20 independent cells were analyzed per condition) (A, right). The numbers of $Rab7^+$ structures with a volume greater than 100 or 50 $nm^3$ in the pericellular and perinuclear zone, respectively, of a given cell are graphed (n=20 cells) (B, C). Scale bars, 500 (A, top and middle panels), 400 (bottom panel) nm.

Referring to FIG. 15A-C, illustrates the chemical structures of compounds including the fluorescent compound 24 (A). (B) Methodology of the compound 24 experiments. (C)

SW480 cells expressing ER-RFP (red) were exposed to 2 μM compound 24 (green) for 1 hour, washed and incubated for the indicated time prior to confocal laser scanning microscopy analysis. Note the progressive accumulation of compound 24 in the perinuclear zone as indicated by an increase in fluorescence intensity (green arrow). The asterisk indicates the fluorescence of compound 24 outside the cell after 1-hour incubation, while the red arrowhead indicates compound 24 inside the NEI. Scale bar, 5 μm (C).

Referring to FIG. 16, illustrates images of the scratch wound healing assay of SW480 cells treated with 10 μM drugs (ICZ, compound 5) without or with EVs ($7.5\times10^8$ particles/ml) derived from SW620 cells for 5 hours (upper panels). The mean±S.E.M. (n=2 independent experiments) is presented (lower panel).

Referring to FIG. 17, illustrates the inhibition of ORP3 by triazole compound 5. Bridging the late endosomes containing the endocytosed EVs (EV) and their cargo to the outer nuclear membrane involves the outer nuclear/ER membrane-associated VAP-A, ORP3 and late endosome-associated Rab7 proteins. The interaction between ORP3 and VAP-A occurs via two specific sequence motifs formed by two phenylalanines in an acidic tract (FFAT) in the ORP3 protein, while a pleckstrin homology (PH) domain mediates its interaction with phosphoinositides in non-ER organelles, including late endosomes. The ORP3 domain engaged in the interaction with Rab7 remains to be defined, but its R-Ras binding site could be involved. The interaction of compound 5 (red) with the C-terminal OSBP-related domain (ORD) of ORP3 (i.e. the hydrophobic pocket that binds to a single sterol) could lead to a conformational change of the protein that would interfere with its interaction with Rab7, and thus abrogate the integrity of the VOR complex.

Referring to FIG. 18A, B, illustrates ICZ and compound 5 that inhibit the transport of HIV-1 integrase into the nucleoplasmic reticulum. (A) HeLa cells were pretreated with 10 μM of drugs as indicated for 30 minutes before HIV-Gag-iGFP infection for 1 hour in the presence of drugs. As controls, DMSO was used (DMSO, HIV-infected cells; control, uninfected cells). Cells were fixed and processed for double immunolabelling for VAP-A and HIV IN (IN-2). They were then observed by confocal laser scanning microscopy, and single x-y optical sections are displayed. The IN-2 immunoreactivity is detected in NEI of DMSO and compound 3-treated cells (white arrow). (B) HeLa cells expressing Rab7-RFP were treated as in panel A, and then double immunolabelled for SUN2 and IN-2. Scale bars, 10 (A) and 5 (B) μm.

Referring to FIG. 19A, B illustrates the quantification of IN-2 immunoreactivity in $SUN2^+$ NEI (A, 50 NEIs were assessed per experiment, n=3, individual values of each experiment is indicated) and the IN-2 nucleoplasm/cytoplasm ratio per cell (B, n=150 cells from three independent experiments) on HeLa cells treated with drugs as indicated (see FIG. 18B). Means±S.D. with individual values for each experiment (A) are shown. N.s., not significant; ***, p<0.001.

Referring to FIG. 20A-C, illustrates the impact of drugs on productive infection. HeLa cells pretreated with drugs as above before HIV-Gag-iGFP infection for 6 hours, washed, and incubated for 24 hours in the presence of drugs. Samples were processed either for immunocytochemistry or flow cytometry analyses. DMSO was used as solvent vehicle. For the immunocytochemistry, fixed cells were labelled for VAP-A and observed by confocal laser scanning microscopy, and single x-y optical sections are displayed (A), while they are trypsinised for flow cytometry (B). Representative fluorescent images and flow histograms from three independent experiments are displayed. Dashed line represents DMSO-treated, noninfected cells as a negative control. Note the reduction in Gag-iGFP expression in cells treated with ICZ and compound 5. The percentage of $GFP^+$ cells as assessed by flow cytometry is plotted (C). Means±S.D. with individual values for each experiment are shown. Cy, cytoplasm; Pm, plasma membrane; n.s., not significant; ***, p<0.001.

Referring to FIG. 21, illustrates the drug toxicity on HeLa cells. Cells were incubated with DMSO solvent alone (control, dashed line), or different concentrations of drugs as indicated for 48 hours. MTS tetrazolium was then added for 1 hour. The absorbance value was measured at 490 nm. The mean±S.D. are shown (n=3).

Modifications to embodiments of the present disclosure described in the foregoing are possible without departing from the scope of the present disclosure as defined by the accompanying claims. Expressions such as "including", "comprising", "incorporating", "have", and "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A compound for use in inhibiting a tripartite VAP-A, ORP3 and Rab7 (VOR) protein complex in multicellular organisms by interfering with at least one mechanism of:

(a) intercellular communication, wherein the intercellular communication is mediated by receptor-ligand interaction and/or extracellular vesicles; and (b) viral infection involving the transport of endocytosed biomaterials to the nucleus of recipient cells, wherein the compound has the following structure

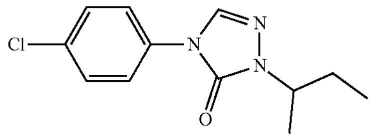

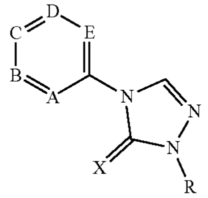

* * * * *